United States Patent
Chin et al.

(10) Patent No.: US 10,086,040 B2
(45) Date of Patent: *Oct. 2, 2018

(54) METHODS FOR TREATING AND PREVENTING CARDIOMYOPATHY WITH A FUSION PROTEIN OF TAFAZZIN AND A CELLULAR PERMEABILITY PEPTIDE

(71) Applicant: University of Washington, Seattle, WA (US)

(72) Inventors: Michael T. Chin, Seattle, WA (US); Wei-Ming Chien, Seattle, WA (US); Ana Dinca, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,012

(22) PCT Filed: Dec. 11, 2015

(86) PCT No.: PCT/US2015/065235
§ 371 (c)(1),
(2) Date: May 18, 2017

(87) PCT Pub. No.: WO2016/094791
PCT Pub. Date: Jun. 16, 2016

(65) Prior Publication Data
US 2017/0360886 A1 Dec. 21, 2017

Related U.S. Application Data

(60) Provisional application No. 62/091,075, filed on Dec. 12, 2014.

(51) Int. Cl.
*A61K 38/45* (2006.01)
*A61P 9/04* (2006.01)
*C07K 14/47* (2006.01)
*A61K 38/17* (2006.01)
*A61K 38/16* (2006.01)
*A61K 38/18* (2006.01)
*A61P 9/00* (2006.01)
*C07K 19/00* (2006.01)
*C07K 7/08* (2006.01)
*C07K 7/06* (2006.01)

(52) U.S. Cl.
CPC ........ *A61K 38/1709* (2013.01); *A61K 38/162* (2013.01); *A61K 38/1767* (2013.01); *A61K 38/1825* (2013.01); *A61K 38/45* (2013.01); *A61P 9/00* (2018.01); *A61P 9/04* (2018.01); *C07K 14/47* (2013.01); *C07K 7/06* (2013.01); *C07K 7/08* (2013.01); *C07K 14/4705* (2013.01); *C07K 14/4716* (2013.01); *C07K 19/00* (2013.01); *C07K 2319/00* (2013.01); *C07K 2319/10* (2013.01)

(58) Field of Classification Search
None
See application file for complete search history.

(56) References Cited

U.S. PATENT DOCUMENTS

| 9,249,184 | B2 | 2/2016 | Robbins et al. |
|---|---|---|---|
| 9,550,981 | B2 | 1/2017 | Chin et al. |
| 2002/0103121 | A1 | 8/2002 | La Thangue et al. |
| 2002/0151004 | A1 | 10/2002 | Craig |
| 2003/0060399 | A1 | 3/2003 | Brophy et al. |
| 2004/0121942 | A1 | 6/2004 | Chien et al. |
| 2006/0251641 | A1 | 11/2006 | Keimel |
| 2007/0135335 | A1 | 6/2007 | Collier et al. |
| 2011/0177051 | A1 | 7/2011 | Galski-Lorberboum et al. |
| 2012/0244136 | A1 | 9/2012 | Robbins et al. |
| 2014/0100128 | A1 | 4/2014 | Narain et al. |
| 2014/0377243 | A1 | 12/2014 | Chung et al. |

FOREIGN PATENT DOCUMENTS

| WO | 2010/017515 | 2/2010 |
|---|---|---|
| WO | 2014/134554 | 9/2014 |

OTHER PUBLICATIONS

Dinca et al, 2015. Journal of Molecular and Cellular Cardiology. 85: S32.*
Acehan, et al., "Cardiac and Skeletal Muscle Defects in a Mouse Model of Human Barth Syndrome," The Journal of Biological Chemistry, vol. 286, No. 2, pp. 899-908, (Nov. 9, 2010).
Acehan, et al., "Distinct effects of tafazzin deletion in differentiated and undifferentiated mitochondria," Mitochondrion, vol. 9, pp. 86-95, (2009).
Aprikyan, et al., "Advances in the understanding of Barth syndrome," British Journal of Haematology, vol. 161, No. 3, pp. 330-338, (Feb. 25, 2013).
Baile, et al., "Unremodeled and Remodeled Cardiolipin Are Functionally Indistinguishable in Yeast," The Journal of Biological Chemistry, vol. 289, No. 3, pp. 1768-1778, (Nov. 27, 2013).
Barth, et al., "An X-Linked Mitochondrial Disease Affecting Cardiac Muscle, Skeletal Muscle and Neutrophil Leucocytes," Journal of the Neurological Sciences, vol. 62, pp. 327-355, (1983).
Barth, et al., "X-linked cardioskeletal myopathy and neutropenia (Barth syndrome) (MIM 302060)," J Inherit Metab Dis, vol. 22, No. 4, pp. 555-567, (1999).

(Continued)

Primary Examiner — Zachary C Howard
(74) Attorney, Agent, or Firm — Stoel Rives LLP; Zhi-Xiang (Alex) Oh

(57) ABSTRACT

Methods for treating patients having a cardiomyopathy are provided. Additionally, methods for prophylactically treating patients at risk of developing a cardiomyopathy are provided. Methods for treating patients having, or at risk of developing, a cardiomyopathy may comprise administering a fusion protein including a tafazzin peptide and a cellular permeability peptide to the patient. Further, the tafazzin peptide may be coupled to the cellular permeability peptide by a polypeptide linker.

20 Claims, 13 Drawing Sheets
Specification includes a Sequence Listing.

(56) References Cited

OTHER PUBLICATIONS

Barth, et al., "X-Linked Cardioskeletal Myopathy and Neutropenia (Barth Syndrome): An Update," American Journal of Medical Genetics, vol. 126A, No. 4, pp. 349-354, (2004).

Barth, et al., "X-linked cardioskeletal myopathy and neutropenia (Barth syndrome): Respiratory-chain abnormalities in cultured fibroblasts," Journal of Inherited Metabolic Disease, vol. 19, No. 2, pp. 157-160, (1996).

Bekeredjian, et al., "Augmentation of Cardiac Protein Delivery Using Ultrasound Targeted Microbubble Destruction," Ultrasound in Medicine & Biology, vol. 31, No. 5, pp. 687-691, (2005).

Bione, et al., "A novel X-linked gene, G4.5. is responsible for Barth syndrome," Nature Genetics, vol. 12, pp. 385-389, (Apr. 1996).

Bleyl, et al., "Xq28-linked Noncompaction of the Left Ventricular Myocardium: Prenatal Diagnosis and Pathologic Analysis of Affected Individuals," American Journal of Medical Genetics, vol. 72, No. 3, pp. 257-265, (1997).

Brandner, et al., "Taz1, an Outer Mitochondrial Membrane Protein, Affects Stability and Assembly of Inner Membrane Protein Complexes: Implications for Barth Syndrome," Molecular Biology of the Cell, vol. 16, No. 11, pp. 5202-5214, (Nov. 2005).

Chin, M.T., "Tafazzin enzyme replacement therapy for heart muscle in Barth syndrome," Abstract only, accessed online at: https://www.barthsyndrome.org/view.asp?ccid=396, 1 page, (retrieved Jan. 5, 2015).

Dai, et al., "Mitochondrial Oxidative Stress Mediates Angiotensin II-Induced Cardiac Hypertrophy and Gαq Overexpression-Induced Heart Failure," Circulation Research, vol. 108, No. 7, pp. 837-846, (2011).

Dudek, et al., "Cardiolipin deficiency affects respiratory chain function and organization in an induced pluripotent stem cell model of Barth syndrome," Stem Cell Research, vol. 11, pp. 806-819, (May 28, 2013).

Frankel, et al., "Cellular Uptake of the Tat Protein from Human Immunodeficiency Virus," Cell, vol. 55, No. 6, pp. 1189-1193, (Dec. 23, 1988).

Geis, et al., "Spatial Distribution of Ultrasound Targeted Microbubble Destruction Increases Cardiac Transgene Expression But Not Capillary Permeability," Ultrasound in Medicine & Biology, vol. 35, No. 7, pp. 1119-1126, (2009).

He, et al., "Tafazzin knockdown interrupts cell cycle progression in cultured neonatal ventricular fibroblasts," Am. J. Physiol. Heart Circ. Physiol., vol. 305, pp. H1332-H1343, (Aug. 30, 2013).

He, Q., "Tafazzin knockdown causes hypertrophy of neonatal ventricular myocytes," American Journal of Physiology Heart and Circulatory Physiology, vol. 299, No. 1, pp. H210-H216, (Mar. 26, 2010).

Houtkooper, et al., "Identification and characterization of human cardiolipin synthase," Federation of European Biochemical Societies Letters, vol. 580, No. 13, pp. 3059-3064, (2006).

Houtkooper, et al., "The enigmatic role of tafazzin in cardiolipin metabolism," Biochimica Biophysica Acta, vol. 1788, No. 10, pp. 2003-2014, (2009).

Khuchua, et al., "A Zebrafish Model of Human Barth Syndrome Reveals the Essential Role of Tafazzin in Cardiac Development and Function," Circulation Research, vol. 99, No. 2, pp. 201-208, (Jul. 21, 2006).

Khuchua, Z., "Impaired fatty-acid metabolism in tafazzin-deficient mice," presented at Jun. 2012 Barth Syndrome Foundation 6th International Scientific, Medical & Family Conference, 26 pages, (Jun. 25-30, 2012).

Kiebish, et al., "Dysfunctional cardiac mitochondrial bioenergetic, lipidomic, and signaling in a murine model of Barth syndrome," Journal of Lipid Research, vol. 54, No. 5, pp. 1312-1325, (Feb. 12, 2013).

Kulik, et al., "Bloodspot Assay Using HPLC-tandem Mass Spectrometry for Detection of Barth Syndrome," Clinical Chemistry, vol. 54, No. 2, pp. 371-378, (2008).

Liao, et al., "Cardiac-Specific Overexpression of GLUT1 Prevents the Development of Heart Failure Attributable to Pressure Overload in Mice," Circulation, vol. 106, No. 16, pp. 2125-2131, (2002).

Lindegger, et al., "Paradoxical SR Ca2+ release in guinea-pig cardiac myocytes after β-adrenergic stimulation revealed by two-photon photolysis of caged Ca2+," J. Physiol., vol. 565 (Pt 3), pp. 801-813, (Mar. 17, 2005).

Liu, et al., "The bHLH transcription factor CHF1/HEY2 regulates susceptibility to apoptosis and heart failure after pressure overload," Am J Physiol Heart Circ Physiol., vol. 298, No. 6, pp. H2082-H2092, (2010).

Liu, et al., "Transcription factor CHF1/Hey2 regulates EC coupling and heart failure in mice through regulation of FKBP12.6," American Journal of Physiology Heart and Circulatory Physiology, vol. 302, No. 9, pp. H1860-H1870, (Mar. 9, 2012).

Mao, et al., "Improved reporter strain for monitoring Cre recombinase-mediated DNA excisions in mice," Proc. Natl. Acad. Sci. USA, vol. 96, pp. 5037-5042, (Apr. 1999).

McCullagh, et al., "Analysis of skeletal muscle function in the C57BL6/SV129 syncoilin knockout mouse," Mammalian Genome, vol. 19, pp. 339-351, (Jul. 2, 2008).

McKenzie, et al., "Mitochondrial Respiratory Chain Supercomplexes Are Destabilized in Barth Syndrome Patients," J Mol. Biol., vol. 361, No. 3, pp. 462-469, (2006).

Min, et al., "Gene delivery using a derivative of the protein transduction domain peptide, K-Antp.," Biomaterials, vol. 31, No. 7, pp. 1858-1864, (2010).

Murphy, et al., "Unraveling the Biological Roles of Reactive Oxygen Species," Cell Metabolism, vol. 13, No. 4, pp. 361-366, (Apr. 6, 2011).

Muzumdar, et al., "A Global Double-Fluorescent Cre Reporter Mouse," Genesis, vol. 45, pp. 593-605, (2007).

Neustein, et al., "An X-Linked Recessive Cardiomyopathy with Abnormal Mitochondria," Pediatrics, vol. 64, No. 1, pp. 24-29, (Jul. 1979).

N'Guessan, et al., "Evaluation of quantitative and qualitative aspects of mitochondrial function in human skeletal and cardiac muscles," Molecular and Cellular Biochemistry, vol. 256/257, No. 1/2, pp. 267-280, (2004).

Oishi, et al., "Myo-mechanical Analysis of Isolated Skeletal Muscle," video article, Journal of Visualized Experiments, 5 pages, (2011).

Pfeiffer, et al., "Cardiolipin Stabilizes Respiratory Chain Supercomplexes," The Journal of Biological Chemistry, vol. 278, No. 52, pp. 52873-52880, (Oct. 15, 2003).

Phoon, et al., "Tafazzin Knockdown in Mice Leads to a Developmental Cardiomyopathy With Early Diastolic Dysfunction Preceding Myocardial Noncompaction," Journal of American Heart Association, vol. 1, No. 2, pp. 1-13, (Apr. 13, 2012).

Pisani, et al., "Enzyme replacement therapy in patients with Fabry disease: State of the art and review of the literature," Molecular Genetics and Metabolism, vol. 107, No. 3, pp. 267-275, (2012).

Pu, W.T., "Modeling Barth Syndrome using Patient-Specific, iPSC-derived Cardiomyocytes," presented at Jun. 2012 Barth Syndrome Foundation International Conf., 73 pages, (2012).

Rapoport, et al., "Successful TAT-mediated enzyme replacement therapy in a mouse model of mitochondrial E3 deficiency," J. Mol. Med., vol. 89, pp. 161-170, (Nov. 16, 2010).

Rapoport, et al., "TAT-mediated Delivery of LAD Restores Pyruvate Dehydrogenase Complex Activity in the Mitochondria of Patients With LAD Deficiency," Molecular Therapy: The Journal of the American Society of Gene Therapy, vol. 16, No. 4, pp. 691-697, (Apr. 2008).

Sag, et al., "Redox regulation of cardiac hypertrophy," Journal of Molecular and Cell Cardiology, vol. 73, pp. 103-111, (2014).

Saks, et al., "Permeabilized cell and skinned fiber techniques in studies of mitochondrial function in vivo," Molecular Cell Biochemistry, vol. 184, pp. 81-100, (1998).

Sambrano, et al., "Navigating the signaling network in mouse cardiac myocytes," Nature, vol. 420, pp. 712-714, (Dec. 12, 2002).

Schlame, et al., "Cardiolipin remodeling and the function of tafazzin," Biochimica et Biophysica Acta, vol. 1831, pp. 582-588, (Nov. 28, 2012).

(56) References Cited

OTHER PUBLICATIONS

Schlame, et al., "Deficiency of Tetralinoleoyl-Cardiolipin in Barth Syndrome," Annals of Neurology, vol. 51, No. 5, pp. 634-637, (2002).

Schlame, et al., "The mechanism of acyl specific phospholipid remodeling by tafazzin," Nature Chemical Biology, vol. 8, No. 10, pp. 862-869, (Jul. 2, 2012).

Schutte, et al., "Annexin V binding assay as a tool to measure apoptosis in differentiated neuronal cells," Journal of Neuroscience Methods, vol. 86, No. 1, pp. 63-69, (1998).

Schwarze, et al., "Protein transduction: unrestricted delivery into all cells?" Trends in Cell Biology, vol. 10, No. 7, pp. 290-295, (Jul. 2000).

Soustek, et al., "Characterization of a Transgenic Short Hairpin RNA-Induced Murine Model of Tafazzin Deficiency," Human Gene Therapy, vol. 22, No. 7, pp. 865-871, (Jul. 2011).

Sparagna, et al., "Loss of cardiac tetralinoleoyl cardiolipin in human and experimental heart failure," Journal of Lipid Research, vol. 48, No. 7, pp. 1559-1570, (Apr. 10, 2007).

Springhorn, et al., "Preproenkephalin mRNA expression in developing rat heart and in cultured ventricular cardiac muscle cells," Biochem J., vol. 258, No. 1, pp. 73-78, (1989).

Stone, et al., "Dose- and Volume Dependent-Response to Intramuscular Injection of Botulinum Neurotoxin-A Optimizes Muscle Force Decrement in Mice," Journal of Orthopaedic Research, vol. 29, pp. 1764-1770, (Apr. 13, 2011).

Thorén, et al., "The Antennapedia peptide penetratin translocates across lipid bilayers—the first direct observation," Federation of European Biochemical Societies Letters, vol. 482, pp. 265-268, (2000).

Valianpour, et al., "Cardiolipin deficiency in X-linked cardioskeletal myopathy and neutropenia (Barth syndrome, MIM 302060): A study in cultured skin fibroblasts," The Journal of Pediatrics, vol. 141, No. 5, pp. 729-733, (Nov. 2002).

Valianpour, et al., "Linoleic acid supplementation of Barth syndrome fibroblasts restores cardiolipin levels: implications for treatment," Journal of Lipid Research, vol. 44, No. 3, pp. 560-566, (Dec. 16, 2002).

Vaz, et al., "Only One Splice Variant of the Human TAZ Gene Encodes a Functional Protein With a Role in Cardiolipin Metabolism," The Journal of Biological Chemistry, vol. 278, No. 44, pp. 43089-43094, (Jun. 5, 2003).

Vermes, et al., "A novel assay for apoptosis Flow cytometric detection of phosphatidylserine expression on early apoptotic cells using fluorescein labelled Annexin V," Journal of Immunological Methods, vol. 184, No. 1, pp. 39-51, (1995).

Wang et al., "Modeling the mitochondrial cardiomyopathy of Barth syndrome with induced pluripotent stem cell and heart-on-chip technologies," Nature Medicine, vol. 20, No. 6, pp. 616-623, (Jun. 2014).

Xiang, et al., "Transcription factor CHF1/Hey2 suppresses cardiac hypertrophy through an inhibitory interaction with GATA4," Am J Physiol Heart Circ Physiol., vol. 290, No. 5, pp. H1997-H2006, (2006).

Xu, et al., "Characterization of Tafazzin Splice Variants from Humans and Fruit Flies," The Journal of Biological Chemistry, vol. 284, No. 42, pp. 29230-29239, (Oct. 16, 2009).

Xu, et al., "Remodeling of Cardiolipin by Phospholipid Transacylation," The Journal of Biological Chemistry, vol. 278, No. 51, pp. 51380-51385, (Oct. 9, 2003).

Xu, et al., "The enzymatic function of tafazzin," The Journal of Biological Chemistry, vol. 281, No. 51, pp. 39217-39224, (Dec. 22, 2006).

Yu, et al., "CHF1/Hey2 Promotes Physiological Hypertrophy in Response to Pressure Overload through Selective Repression and Activation of Specific Transcriptional Pathways," OMICS a Journal of Integrative Biology, vol. 13, No. 6, pp. 501-511, (Nov. 6, 2009).

Zahid, et al., "Identification of a Cardiac Specific Protein Transduction Domain by In Vivo Biopanning Using a M13 Phage Peptide Display Library in Mice," PLoS One, vol. 5, No. 8, e12252, pp. 1-11, (Aug. 2010).

Zhang, et al., "Cardiolipin Is Essential for Organization of Complexes III and IV Into a Supercomplex in Intact Yeast Mitochondria," The Journal of Biological Chemistry, vol. 280, No. 33, pp. 29403-29408, (Aug. 19, 2005).

Zhang, et al., "Gluing the Respiratory Chain Together: Cardiolipin Is Required for Supercomplex Formation in the Inner Mitochondrial Membrane," The Journal of Biological Chemistry, vol. 277, No. 46, pp. 43553-43556, (Oct. 2, 2002).

Zhou, et al., "Generation of Induced Pluripotent Stem Cells Using Recombinant Proteins," Cell Stem Cell, vol. 4, No. 5, pp. 381-384, (May 8, 2009).

Zhou, et al., "Inducible and Reversible Transgene Expression in Human Stem Cells After Efficient and Stable Gene Transfer," Stem Cells, vol. 25, pp. 779-789, (2007).

Zhu, et al., "Local Control of Excitation-Contraction Coupling in Human Embryonic Stem Cell-Derived Cardiomyocytes," PLoS One, vol. 4, No. 4, e5407, 11 pages, (Apr. 2009).

International Search Report and Written Opinion dated Apr. 1, 2016 in International Patent Application No. PCT/US2015/065235.

U.S. Appl. No. 14/603,141, Feb. 24, 2016, Office Action.

U.S. Appl. No. 14/603,141, May 24, 2016, Response to Office Action.

U.S. Appl. No. 14/603,141, Sep. 8, 2016, Notice of Allowance.

* cited by examiner

SEQUENCE LISTING

<160> NUMBER OF SEQ ID NOS: 13

<210> SEQ ID NO 1
<211> LENGTH: 292
<212> TYPE: PRT
<213> ORGANISM: Homo sapiens

<400> SEQUENCE: 1

```
Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Ala Glu Phe Phe
        115                 120                 125

Gln Ala Glu Asn Glu Gly Lys Gly Val Leu Asp Thr Gly Arg His Met
    130                 135                 140

Pro Gly Ala Gly Lys Arg Arg Glu Lys Gly Asp Gly Val Tyr Gln Lys
145                 150                 155                 160

Gly Met Asp Phe Ile Leu Glu Lys Leu Asn His Gly Asp Trp Val His
                165                 170                 175

Ile Phe Pro Glu Gly Lys Val Asn Met Ser Ser Glu Phe Leu Arg Phe
            180                 185                 190

Lys Trp Gly Ile Gly Arg Leu Ile Ala Glu Cys His Leu Asn Pro Ile
        195                 200                 205
```

Ile Leu Pro Leu Trp His Val Gly Met Asn Asp Val Leu Pro Asn Ser
    210                 215                 220

Pro Pro Tyr Phe Pro Arg Phe Gly Gln Lys Ile Thr Val Leu Ile Gly
225                 230                 235                 240

Lys Pro Phe Ser Ala Leu Pro Val Leu Glu Arg Leu Arg Ala Glu Asn
                245                 250                 255

Lys Ser Ala Val Glu Met Arg Lys Ala Leu Thr Asp Phe Ile Gln Glu
                260                 265                 270

Glu Phe Gln His Leu Lys Thr Gln Ala Glu Gln Leu His Asn His Leu
                275                 280                 285

Gln Pro Gly Arg
    290

<210> SEQ ID NO 2
<211> LENGTH: 262
<212> TYPE: PRT
<213> ORGANISM: Homo sapiens

<400> SEQUENCE: 2

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
                20                  25                  30

Cys Phe Trp Thr Lys Tyr Met Asn His Leu Thr Val His Asn Arg Glu
            35                  40                  45

Val Leu Tyr Glu Leu Ile Glu Lys Arg Gly Pro Ala Thr Pro Leu Ile
50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Ala Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln His Leu Lys Thr Gln Ala Glu Gln Leu His Asn
                245                 250                 255

His Leu Gln Pro Gly Arg
                260

```
<210> SEQ ID NO 3
<211> LENGTH: 262
<212> TYPE: PRT
<213> ORGANISM: Mus musculus

<400> SEQUENCE: 3

Met Pro Leu His Val Lys Trp Pro Phe Pro Ala Val Pro Arg Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Lys Glu
        35                  40                  45

Val Leu Tyr Glu Leu Ile Glu Asn Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Thr Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
                245                 250                 255

His Phe Gln Pro Gly Arg
            260

<210> SEQ ID NO 4
<211> LENGTH: 262
<212> TYPE: PRT
<213> ORGANISM: Artificial Sequence
<220> FEATURE:
<223> OTHER INFORMATION: Human-mouse chimeric protein

<400> SEQUENCE: 4

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
        35                  40                  45

Val Leu Tyr Glu Leu Ile Glu Lys Arg Gly Pro Ala Thr Pro Leu Ile
    50                  55                  60
```

-continued

```
Thr Val Ser Asn His Gln Ser Cys Met Asp Asp Pro His Leu Trp Gly
 65                  70                  75                  80

Ile Leu Lys Leu Arg His Ile Trp Asn Leu Lys Leu Met Arg Trp Thr
                 85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Thr Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
                245                 250                 255

His Phe Gln Pro Gly Arg
            260
```

<210> SEQ ID NO 5
<211> LENGTH: 262
<212> TYPE: PRT
<213> ORGANISM: Artificial Sequence
<220> FEATURE:
<223> OTHER INFORMATION: Mouse-human chimeric protein

<400> SEQUENCE: 5

```
Met Pro Leu His Val Lys Trp Pro Phe Pro Ala Val Pro Pro Leu Thr
  1               5                  10                  15

Trp Thr Leu Ala Ser Ser Val Val Met Gly Leu Val Gly Thr Tyr Ser
                 20                  25                  30

Cys Phe Trp Thr Lys Tyr Met Asn His Leu Thr Val His Asn Arg Glu
             35                  40                  45

Val Leu Tyr Glu Leu Ile Glu Lys Arg Gly Pro Ala Thr Pro Leu Ile
         50                 55                  60

Thr Val Ser Asn His Gln Ser Cys Met Asp Asp Pro His Leu Trp Gly
 65                  70                  75                  80

Ile Leu Lys Leu Arg His Ile Trp Asn Leu Lys Leu Met Arg Trp Thr
                 85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160
```

```
Arg Phe Lys Trp Gly Ile Gly Arg Leu Ile Ala Glu Cys His Leu Asn
            165                 170                 175

Pro Ile Ile Leu Pro Leu Trp His Val Gly Met Asn Asp Val Leu Pro
            180                 185                 190

Asn Ser Pro Tyr Phe Pro Arg Phe Gly Gln Lys Ile Thr Val Leu
            195                 200                 205

Ile Gly Lys Pro Phe Ser Thr Leu Pro Val Leu Glu Arg Leu Arg Ala
        210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
            245                 250                 255

His Phe Gln Pro Gly Arg
            260

<210> SEQ ID NO 6
<211> LENGTH: 16
<212> TYPE: PRT
<213> ORGANISM: Artificial Sequence
<220> FEATURE:
<223> OTHER INFORMATION: Antennapedia permeability peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: HIV Tat permeability peptide

<400> SEQUENCE: 7

Tyr Gly Arg Lys Lys Arg Arg Gln Arg Arg Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Cardiac Targeting Peptide (CTP)

<400> SEQUENCE: 8

Ala Pro Trp His Leu Ser Ser Gln Tyr Ser Arg Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Kaposi FGF4-derived peptide

<400> SEQUENCE: 9

Ala Ala Val Leu Leu Pro Val Leu Leu Ala Ala Pro
1               5                   10

<210> SEQ ID NO 10
<211> LENGTH: 291
<212> TYPE: PRT
<213> ORGANISM: Artificial Sequence
```

```
<220> FEATURE:
<223> OTHER INFORMATION: Mouse TAZ-Antp

<400> SEQUENCE: 10

Met Pro Leu His Val Lys Trp Pro Phe Pro Ala Val Pro Arg Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Lys Glu
        35                  40                  45

Val Leu Tyr Glu Leu Ile Glu Asn Arg Gly Pro Ala Thr Pro Leu Ile
    50                  55                  60

Thr Val Ser Asn His Gln Ser Cys Met Asp Asp Pro His Leu Trp Gly
65                  70                  75                  80

Ile Leu Lys Leu Arg His Ile Trp Asn Leu Lys Leu Met Arg Trp Thr
                85                  90                  95

Pro Ala Ala Ala Asp Ile Cys Phe Thr Lys Glu Leu His Ser His Phe
            100                 105                 110

Phe Ser Leu Gly Lys Cys Val Pro Val Cys Arg Gly Asp Gly Val Tyr
        115                 120                 125

Gln Lys Gly Met Asp Phe Ile Leu Glu Lys Leu Asn His Gly Asp Trp
    130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Thr Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln Arg Leu Lys Met Gln Ala Glu Gln Leu His Asn
                245                 250                 255

His Phe Gln Pro Gly Arg Leu Glu Glu Ser Gly Gly Gly Gly Ser Arg
            260                 265                 270

Gln Ile Lys Ile Trp Phe Gln Asn Arg Arg Met Lys Trp Lys Lys Gly
        275                 280                 285

Ser Gly Cys
    290

<210> SEQ ID NO 11
<211> LENGTH: 291
<212> TYPE: PRT
<213> ORGANISM: Artificial Sequence
<220> FEATURE:
<223> OTHER INFORMATION: Human TAZ-Antp

<400> SEQUENCE: 11

Met Pro Leu His Val Lys Trp Pro Phe Pro Ala Val Pro Pro Leu Thr
1               5                   10                  15

Trp Thr Leu Ala Ser Ser Val Val Met Gly Leu Val Gly Thr Tyr Ser
            20                  25                  30

Cys Phe Trp Thr Lys Tyr Met Asn His Leu Thr Val His Asn Arg Glu
```

```
                    35                  40                  45
Val Leu Tyr Glu Leu Ile Glu Lys Arg Gly Pro Ala Thr Pro Leu Ile
 50                  55                  60

Thr Val Ser Asn His Gln Ser Cys Met Asp Asp Pro His Leu Trp Gly
 65                  70                  75                  80

Ile Leu Lys Leu Arg His Ile Trp Asn Leu Lys Leu Met Arg Trp Thr
                 85                  90                  95

Pro Ala Ala Ala Asp Ile Cys Phe Thr Lys Glu Leu His Ser His Phe
                100                 105                 110

Phe Ser Leu Gly Lys Cys Val Pro Val Cys Arg Gly Asp Gly Val Tyr
            115                 120                 125

Gln Lys Gly Met Asp Phe Ile Leu Glu Lys Leu Asn His Gly Asp Trp
        130                 135                 140

Val His Ile Phe Pro Glu Gly Lys Val Asn Met Ser Ser Glu Phe Leu
145                 150                 155                 160

Arg Phe Lys Trp Gly Ile Gly Arg Leu Ile Ala Glu Cys His Leu Asn
                165                 170                 175

Pro Ile Ile Leu Pro Leu Trp His Val Gly Met Asn Asp Val Leu Pro
            180                 185                 190

Asn Ser Pro Pro Tyr Phe Pro Arg Phe Gly Gln Lys Ile Thr Val Leu
        195                 200                 205

Ile Gly Lys Pro Phe Ser Ala Leu Pro Val Leu Glu Arg Leu Arg Ala
    210                 215                 220

Glu Asn Lys Ser Ala Val Glu Met Arg Lys Ala Leu Thr Asp Phe Ile
225                 230                 235                 240

Gln Glu Glu Phe Gln His Leu Lys Thr Gln Ala Glu Gln Leu His Asn
                245                 250                 255

His Leu Gln Pro Gly Arg Val Glu Glu Ser Gly Gly Gly Ser Arg
            260                 265                 270

Gln Ile Lys Ile Trp Phe Gln Asn Arg Arg Met Lys Trp Lys Lys Gly
        275                 280                 285

Ser Gly Cys
    290

<210> SEQ ID NO 12
<211> LENGTH: 288
<212> TYPE: PRT
<213> ORGANISM: Artificial Sequence
<220> FEATURE:
<223> OTHER INFORMATION: Mouse TAZ-CTP

<400> SEQUENCE: 12

Met Pro Leu His Val Lys Trp Pro Phe Pro Ala Val Pro Arg Leu Thr
 1               5                  10                  15

Trp Thr Leu Ala Ser Ser Val Val Met Gly Leu Val Gly Thr Tyr Ser
                20                  25                  30

Cys Phe Trp Thr Lys Tyr Met Asn His Leu Thr Val His Asn Lys Glu
            35                  40                  45

Val Leu Tyr Glu Leu Ile Glu Asn Arg Gly Pro Ala Thr Pro Leu Ile
 50                  55                  60

Thr Val Ser Asn His Gln Ser Cys Met Asp Asp Pro His Leu Trp Gly
 65                  70                  75                  80

Ile Leu Lys Leu Arg His Ile Trp Asn Leu Lys Leu Met Arg Trp Thr
                 85                  90                  95

Pro Ala Ala Ala Asp Ile Cys Phe Thr Lys Glu Leu His Ser His Phe
```

```
              100                 105                 110
Phe Ser Leu Gly Lys Cys Val Pro Val Cys Arg Gly Asp Gly Val Tyr
        115                 120                 125
Gln Lys Gly Met Asp Phe Ile Leu Glu Lys Leu Asn His Gly Asp Trp
        130                 135                 140
Val His Ile Phe Pro Glu Gly Lys Val Asn Met Ser Ser Glu Phe Leu
145                 150                 155                 160
Arg Phe Lys Trp Gly Ile Gly Arg Leu Ile Ala Glu Cys His Leu Asn
        165                 170                 175
Pro Ile Ile Leu Pro Leu Trp His Val Gly Met Asn Asp Val Leu Pro
        180                 185                 190
Asn Ser Pro Pro Tyr Phe Pro Arg Phe Gly Gln Lys Ile Thr Val Leu
        195                 200                 205
Ile Gly Lys Pro Phe Ser Thr Leu Pro Val Leu Glu Arg Leu Arg Ala
        210                 215                 220
Glu Asn Lys Ser Ala Val Glu Met Arg Lys Ala Leu Thr Asp Phe Ile
225                 230                 235                 240
Gln Glu Glu Phe Gln Arg Leu Lys Met Gln Ala Glu Gln Leu His Asn
        245                 250                 255
His Phe Gln Pro Gly Arg Leu Glu Ser Gly Gly Gly Ser Pro Gly
        260                 265                 270
Ala Pro Trp His Leu Ser Ser Gln Tyr Ser Arg Thr Gly Ser Gly Cys
        275                 280                 285
```

<210> SEQ ID NO 13
<211> LENGTH: 318
<212> TYPE: PRT
<213> ORGANISM: Artificial Sequence
<220> FEATURE:
<223> OTHER INFORMATION: Human TAZ-CTP

<400> SEQUENCE: 13

```
Met Pro Leu His Val Lys Trp Pro Phe Pro Ala Val Pro Pro Leu Thr
1               5                   10                  15
Trp Thr Leu Ala Ser Ser Val Val Met Gly Leu Val Gly Thr Tyr Ser
        20                  25                  30
Cys Phe Trp Thr Lys Tyr Met Asn His Leu Thr Val His Asn Arg Glu
        35                  40                  45
Val Leu Tyr Glu Leu Ile Glu Lys Arg Gly Pro Ala Thr Pro Leu Ile
        50                  55                  60
Thr Val Ser Asn His Gln Ser Cys Met Asp Asp Pro His Leu Trp Gly
65                  70                  75                  80
Ile Leu Lys Leu Arg His Ile Trp Asn Leu Lys Leu Met Arg Trp Thr
        85                  90                  95
Pro Ala Ala Ala Asp Ile Cys Phe Thr Lys Glu Leu His Ser His Phe
        100                 105                 110
Phe Ser Leu Gly Lys Cys Val Pro Val Cys Arg Gly Ala Glu Phe Phe
        115                 120                 125
Gln Ala Glu Asn Glu Gly Lys Gly Val Leu Asp Thr Gly Arg His Met
        130                 135                 140
Pro Gly Ala Gly Lys Arg Arg Glu Lys Gly Asp Gly Val Tyr Gln Lys
145                 150                 155                 160
Gly Met Asp Phe Ile Leu Glu Lys Leu Asn His Gly Asp Trp Val His
        165                 170                 175
Ile Phe Pro Glu Gly Lys Val Asn Met Ser Ser Glu Phe Leu Arg Phe
```

-continued

```
                180                    185                    190
Lys Trp Gly Ile Gly Arg Leu Ile Ala Glu Cys His Leu Asn Pro Ile
        195                    200                    205

Ile Leu Pro Leu Trp His Val Gly Met Asn Asp Val Leu Pro Asn Ser
        210                    215                    220

Pro Pro Tyr Phe Pro Arg Phe Gly Gln Lys Ile Thr Val Leu Ile Gly
225             230                    235                    240

Lys Pro Phe Ser Ala Leu Pro Val Leu Glu Arg Leu Arg Ala Glu Asn
                245                    250                    255

Lys Ser Ala Val Glu Met Arg Lys Ala Leu Thr Asp Phe Ile Gln Glu
                260                    265                    270

Glu Phe Gln His Leu Lys Thr Gln Ala Glu Gln Leu His Asn His Leu
            275                    280                    285

Gln Pro Gly Arg Val Glu Ser Gly Gly Gly Ser Pro Gly Ala Pro
        290                    295                    300

Trp His Leu Ser Ser Gln Tyr Ser Arg Thr Gly Ser Gly Cys
305                 310                    315
```

METHODS FOR TREATING AND PREVENTING CARDIOMYOPATHY WITH A FUSION PROTEIN OF TAFAZZIN AND A CELLULAR PERMEABILITY PEPTIDE

CROSS-REFERENCE TO RELATED APPLICATIONS

This application is a 371 National Phase Application of International Application No. PCT/US2015/065235 filed on Dec. 11, 2015, which claims the benefit of and priority to U.S. Provisional Patent Application No. 62/091,075 filed on Dec. 12, 2014, all of which are incorporated herein by reference.

TECHNICAL FIELD

The present disclosure relates generally to methods of using fusion proteins comprising a tafazzin peptide and a cellular permeability peptide to treat a subject having a cardiomyopathy. The present disclosure also relates to use of fusion proteins comprising a tafazzin peptide and a cellular permeability peptide in prophylaxis against developing a cardiomyopathy in a subject at risk of developing such a disorder. In particular, the present disclosure relates to methods of using fusion proteins comprising a tafazzin peptide coupled to a cellular permeability peptide by a polypeptide linker.

BACKGROUND

Barth syndrome is an X-linked disorder that can result from defects in the gene encoding tafazzin, an acyltransferase that can modify cardiolipin to a tetralinoleoyl form and that can be involved in mitochondrial respiration. The clinical manifestations of Barth syndrome may include, but are not limited to, muscular hypotonia, cardiomyopathy, and neutropenia.

In Barth syndrome, a single gene mutation in the mitochondrial transacylase, TAZ, can result in impairment of lipid metabolism (see Aprikyan A A and Khuchua Z, Brit J Haematol, 2013; 161(3):330-8) leading to mitochondrial dysfunction, which is manifested clinically in highly energetic tissues such as the heart and skeletal muscle (see Aprikyan A A and Khuchua Z, Brit J Haematol, 2013; 161(3):330-8 and Khuchua Z, et al., Circ Res, 2006; 99(2): 201-8). TAZ can catalyze the transfer of acyl chains from phosphatidyl choline to cardiolipin (CL), remodeling monolysocardiolipin (MLCL) to tetralinoleoyl cardiolipin (L4CL) (see Houtkooper R H, et al., Biochim Biophys Acta, 2009; 1788(10):2003-14 and Xu Y, et al., J Biol Chem, 2003; 278(51):51380-5). Barth syndrome patients exhibit a reduction in the levels of L4CL and an accumulation of MLCL (see Xu Y, et al. J Biol Chem, 2006; 281(51):39217-24), which can lead to mitochondrial dysfunction. These patients may experience growth deficiencies, exercise intolerance, cardiomyopathy, hypotonia, neutropenia, etc. (see Barth P G, et al., Am J Med Genet Part A, 2004; 126A(4):349-54).

One of the leading causes of morbidity among Barth syndrome patients is cardiac failure. Patients may exhibit endomyocardial fibroelastosis, dilated cardiomyopathy, and, as often observed with mitochondrial disorders, hypertrabeculation. At the cellular level, hearts from affected patients may demonstrate morphologically abnormal mitochondria (see Neustein H B, et al., Pediatrics, 1979; 64(1):24-9) while fibroblasts may demonstrate a deficiency of respiratory complexes (see Barth P G, et al., J Inherit Metab Dis, 1999; 22(4):555-67) and a decrease in oxygen consumption rates (see Houtkooper R H, et al., Biochim Biophys Acta, 2009; 1788(10):2003-14). CL, a structurally unique phospholipid component of the inner mitochondrial membrane, can provide functional support for the electron transport chain complexes (see Kiebish M A, et al., J Lipid Res, 2013; 54(5):1312-25 and Pfeiffer K, et al., J Biol Chem, 2003; 278(52):52873-80). In the absence of CL, respiratory supercomplex formation may be hindered (McKenzie M, et al., J Mol Biol, 2006; 361(3):462-914) and individual complex activity may be decreased (see Zhang M, et al., J Biol Chem, 2005; 280(33):29403-8). Disturbances in the acyl chain composition of CL have been linked to impaired mitochondrial respiratory function (see Xu Y, et al., J Biol Chem, 2003; 278(51):51380-5), possibly through alteration in membrane dynamics (see Baile M G, et al., J Biol Chem, 2014; 289(3): 1768-78).

Since mitochondrial respiration is responsible for ATP generation, it has long been assumed that the cardiac and skeletal myopathy seen in Barth syndrome is a result of diminished ATP generation and depleted ATP stores. Recently, it has been reported that cardiomyocytes (CMs) derived from induced pluripotent stem cells (iPS cells) containing targeted TAZ mutations demonstrate normal ATP stores but increased reactive oxygen species (ROS), suggesting that the pathogenesis of Barth syndrome may be due to ROS generation (see Wang G, et al., Nat Med, 2014; 20(6):616-23). ROS have long been implicated in the pathogenesis of cardiac hypertrophy and regulation of excitation-contraction coupling through effects on specific signaling pathways such as ERK, AKT, and PKA (see Sag C M, et al., J Mol Cell Cardiol, 2014; 73C:103-11). Mitochondrial ROS, in particular, have been associated with angiotensin II-induced hypertrophy and heart failure associated with Gaq signaling (see Dai D F, et al., Circ Res 2011; 108(7):837-46). Excessive ROS have also been linked to apoptosis (see Murphy M P, et al., Cell Metab, 2011; 13(4):361-6).

Additionally, there are other indications associated with a tafazzin deficiency and remodeled cardiolipin deficiency. These indications include, but are not limited to, dilated cardiomyopathy, hypertrophic cardiomyopathy, noncompaction cardiomyopathy, ischemic cardiomyopathy, hypertensive cardiomyopathy, diabetic cardiomyopathy, and chemotherapy induced cardiomyopathy. The mitochondrial phospholipid cardiolipin can be involved in optimal, or substantially optimal, mitochondrial respiration, and loss of mitochondrial phospholipid cardiolipin can be associated with the development of heart failure (see Sparagna G C, et al., J Lipid Res, 2007; 48(7):1559-70).

BRIEF DESCRIPTION OF THE DRAWINGS

The embodiments disclosed herein will become more fully apparent from the following description and appended claims, taken in conjunction with the accompanying drawings.

DETAILED DESCRIPTION

Figure 1A:
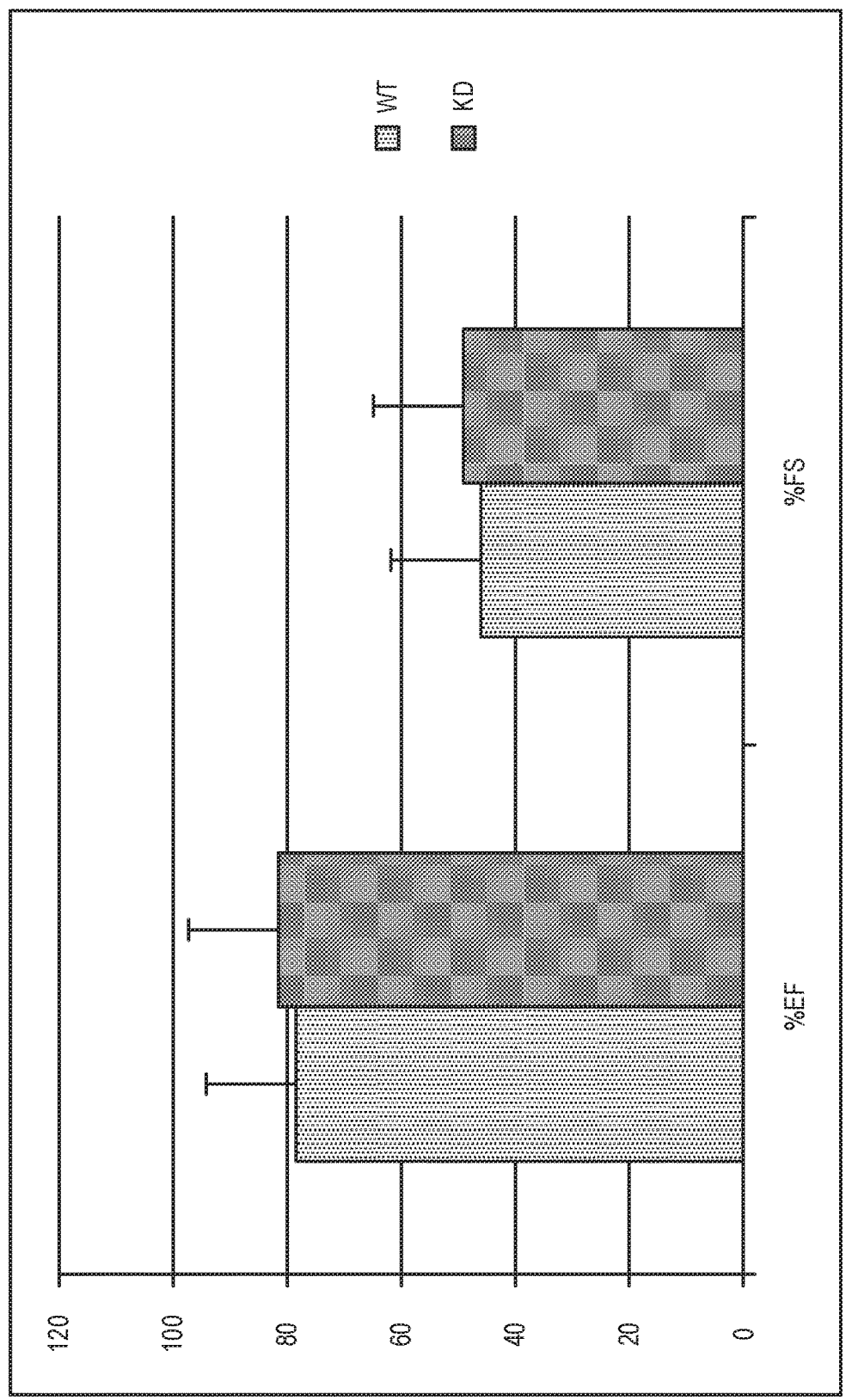
FIG. 1A is a graph depicting ejection fraction (% EF) and fractional shortening (% FS) in wild-type (WT) and TAZ-knockdown (KD) mice at 8 weeks of age. As depicted, TAZ-KD mice show normal ejection fraction and fractional shortening at 8 weeks of age.

The present disclosure relates generally to methods for treating a subject having a cardiomyopathy. The present disclosure also relates to methods for prophylactically treating a subject at risk of developing a cardiomyopathy. The methods for treating a subject having, or at risk of developing, a cardiomyopathy may comprise administering to the subject a fusion protein including a tafazzin peptide and a cellular permeability peptide. The methods for treating a subject having, or at risk of developing, a cardiomyopathy may also comprise identifying a subject having a tafazzin gene (TAZ) mutation.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, "tafazzin" refers to a phospholipid-lysophospholipid transacylase that can be responsible for modification of cardiolipin (a membrane phospholipid) to its tetralinoleoyl form. In some embodiments, tafazzin can refer to full-length human tafazzin or human tafazzin lacking exon 5, both of which exhibit transacylase activity. In certain embodiments, tafazzin can refer to full-length mouse tafazzin, which is homologous to the human tafazzin lacking exon 5.

As used herein, "peptide" and "polypeptide" are used in their broadest senses to refer to a sequence of subunit amino acids. The peptides or polypeptides of the invention may comprise L-amino acids, D-amino acids (which can be resistant to L-amino acid-specific proteases in vivo), or a combination of D- and L-amino acids. The terms peptide and polypeptide can be used interchangeably. The peptides and polypeptides described herein may be chemically synthesized or recombinantly expressed. The peptides and polypeptides may be linked to any other moiety as deemed useful for a given purpose. Such linkage can comprise covalent linkages or non-covalent linkages as is understood by those of skill in the art.

As used herein, "fusion proteins" or "chimeric proteins" refer to proteins created through the joining of two or more genes (e.g., a fusion gene), each of which originally coded for separate proteins. Translation of this fusion gene may result in one or more polypeptides comprising functional properties derived from each of the two or more genes.

As used herein, a "cellular permeability peptide" is a peptide that facilitates cellular uptake of the peptide itself and other peptides that are linked to the cellular permeability peptide. In certain embodiments, these peptides can comprise portions of *Drosophila* antennapedia, HIV Tat, cardiac targeting, and Kaposi FGF4 peptides, which may facilitate cellular uptake. As used herein, such peptide fragments may be referred to as antennapedia permeability peptides, HIV Tat permeability peptides, cardiac targeting permeability peptides, and Kaposi FGF4 permeability peptides.

Amino acid residues as disclosed herein can be modified by conservative substitutions to maintain, or substantially maintain, overall polypeptide structure and/or function. As used here, "conservative amino acid substitution" indicates that: hydrophobic amino acids (i.e., Ala, Cys, Gly, Pro, Met, Sce, Sme, Val, Ile, and Leu) can be substituted with other hydrophobic amino acids; hydrophobic amino acids with bulky side chains (i.e., Phe, Tyr, and Trp) can be substituted with other hydrophobic amino acids with bulky side chains; amino acids with positively charged side chains (i.e., Arg, His, and Lys) can be substituted with other amino acids with positively charged side chains; amino acids with negatively charged side chains (i.e., Asp and Glu) can be substituted with other amino acids with negatively charged side chains; and amino acids with polar uncharged side chains (i.e., Ser, Thr, Asn, and Gln) can be substituted with other amino acids with polar uncharged side chains.

Treating a subject can comprise delivering an effective amount or delivering a prophylactic treatment and/or a therapeutic treatment to a subject (e.g., a patient). An "effective amount" is an amount of a compound that can result in a desired physiological change in a subject. Effective amounts may also be administered for research purposes.

A "prophylactic treatment" comprises a treatment administered to a subject who does not display signs or symptoms of a disease or condition, or a subject who displays only early signs or symptoms of a disease or condition, such that treatment is administered for the purpose of diminishing, preventing, and/or decreasing the risk of further developing the disease or condition or of diminishing, preventing, and/or decreasing the risk of developing the disease or condition. Thus, a prophylactic treatment may function as a preventative treatment against a disease or condition.

A "therapeutic treatment" comprises a treatment administered to a subject who displays symptoms or signs of a disease or a condition and the therapeutic treatment is administered to the subject for the purpose of diminishing or eliminating the symptoms or the signs of the disease or the condition.

"Therapeutically effective amounts" comprise amounts that provide prophylactic treatment and/or therapeutic treatment. Therapeutically effective amounts need not fully prevent or cure the disease or the condition but can also provide a partial benefit, such as a delay of onset or an alleviation or an improvement of at least one symptom of the disease or the condition.

For administration, effective amounts and therapeutically effective amounts (also referred to herein as doses) can be initially estimated based on results from in vitro assays and/or animal model studies. For example, a dose can be formulated in animal models to achieve a circulating concentration range that includes the $IC_{50}$ as determined in cell culture. Such information can be used to more accurately determine useful doses in subjects of interest.

The actual dose amount administered to a particular subject can be determined by a physician, a veterinarian, or a researcher, taking into account parameters such as, but not limited to, physical and physiological factors including body weight, severity of condition, type of disease, previous or concurrent therapeutic interventions, idiopathy of the subject, and/or route of administration.

Doses can range from 0.1 mg/kg/day to 5 mg/kg/day, from 0.5 mg/kg/day to 1 mg/kg/day, from 0.1 mg/kg/day to 5 µg/kg/day, or from 0.5 mg/kg/day to 1 µg/kg/day. In other non-limiting examples, a dose can comprise 1 µg/kg/day, 5 µg/kg/day, 10 µg/kg/day, 50 µg/kg/day, 100 µg/kg/day, 200 µg/kg/day, 350 µg/kg/day, 500 µg/kg/day, 1 mg/kg/day, 5 mg/kg/day, 10 mg/kg/day, 50 mg/kg/day, 100 mg/kg/day, 200 mg/kg/day, 350 mg/kg/day, 500 mg/kg/day, or 1000 mg/kg/day. Therapeutically effective amounts can be achieved by administering single or multiple doses during the course of a treatment regimen (i.e., days, weeks, months, etc.).

In some embodiments, at least one compound is provided as part of a pharmaceutical composition. The pharmaceutical composition can comprise, for example, at least 0.1% w/v of a compound. In other embodiments, the pharmaceutical composition can comprise between 2% and 75% of compound per weight of the pharmaceutical composition, or between 25% and 60% of compound per weight of the pharmaceutical composition.

Pharmaceutically acceptable salts, tautomers, and isomers of the compounds disclosed herein can also be used. Exemplary salts can include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The formulations described herein can be administered by, without limitation, injection, inhalation, infusion, perfusion, lavage, and/or ingestion. Routes of administration can include, but are not limited to, intravenous, intradermal, intraarterial, intraperitoneal, intralesional, intracranial, intraarticular, intraprostatic, intrapleural, intratracheal, intranasal, intravitreal, intravaginal, intrarectal, topical, intratumoral, intramuscular, intravesicular, intrapericardial, intraumbilical, intraocularal, mucosal, oral, subcutaneous, and/or subconjunctival.

In some embodiments, for injection, formulations can be made as aqueous solutions, such as in buffers including, but not limited to, Hanks' solution, Ringer's solution, and/or physiological saline. The solutions can contain formulatory agents such as suspending, stabilizing, and/or dispersing agents. Alternatively, the formulation can be in lyophilized and/or powder form for constitution with a suitable vehicle control (e.g., sterile pyrogen-free water) before use.

Any formulation disclosed herein can advantageously comprise any other pharmaceutically acceptable carrier or carriers, which comprise those that do not produce significantly adverse, allergic, or other untoward reactions that may outweigh the benefit of administration, whether for research, prophylactic, and/or therapeutic treatments. Exemplary pharmaceutically acceptable carriers and formulations are disclosed in Remington's Pharmaceutical Sciences, 18th Ed., Mack Printing Company, 1990, which is incorporated by reference herein for its teachings regarding the same. Moreover, formulations can be prepared to meet sterility, pyrogenicity, general safety, and purity standards as required by the United States FDA's Division of Biological Standards and Quality Control and/or other relevant U.S. and foreign regulatory agencies.

Exemplary, generally used, pharmaceutically acceptable carriers may comprise, but are not limited to, bulking agents or fillers, solvents or co-solvents, dispersion media, coatings, surfactants, antioxidants (e.g., ascorbic acid, methionine, and vitamin E), preservatives, isotonic agents, absorption delaying agents, salts, stabilizers, buffering agents, chelating agents (e.g., EDTA), gels, binders, disintegration agents, and/or lubricants.

Exemplary buffering agents may comprise, but are not limited to, citrate buffers, succinate buffers, tartrate buffers, fumarate buffers, gluconate buffers, oxalate buffers, lactate buffers, acetate buffers, phosphate buffers, histidine buffers, and/or trimethylamine salts.

Exemplary preservatives may comprise, but are not limited to, phenol, benzyl alcohol, meta-cresol, methylparaben, propyl paraben, octadecyldimethylbenzyl ammonium chloride, benzalkonium halides, hexamethonium chloride, alkyl parabens (such as methyl or propyl paraben), catechol, resorcinol, cyclohexanol, and/or 3-pentanol.

Exemplary isotonic agents may comprise polyhydric sugar alcohols comprising, but not limited to, trihydric or higher sugar alcohols, (e.g., glycerin, erythritol, arabitol, xylitol, sorbitol, and/or mannitol).

Exemplary stabilizers may comprise, but are not limited to, organic sugars, polyhydric sugar alcohols, polyethylene glycol, sulfur-containing reducing agents, amino acids, low molecular weight polypeptides, proteins, immunoglobulins, hydrophilic polymers, and/or polysaccharides.

Formulations can also be depot preparations. In some embodiments, such long-acting formulations may be administered by, without limitation, implantation (e.g., subcutaneously or intramuscularly) or by intramuscular injection. Thus, for example, compounds can be formulated with suitable polymeric and/or hydrophobic materials (e.g., as an emulsion in an acceptable oil) or ion exchange resins, or as sparingly soluble derivatives (e.g., as a sparingly soluble salt).

Additionally, in various embodiments, compounds can be delivered using sustained-release systems, such as semipermeable matrices of solid polymers comprising at least one compound. Various sustained-release materials have been established and are well known by those of ordinary skill in the art. Sustained-release capsules may, depending on their chemical nature, release the compound following administration for a few weeks up to over 100 days.

A first aspect of the disclosure relates to methods for treating, or methods for therapeutic treatment of, a subject or patient having cardiomyopathy. The cardiomyopathy may be selected from at least one of chemotherapy-induced cardiomyopathy, diabetic cardiomyopathy, dilated cardiomyopathy, hypertensive cardiomyopathy, hypertrophic cardiomyopathy, ischemic cardiomyopathy, and/or noncompaction cardiomyopathy. For example, the methods may comprise treating a subject having dilated cardiomyopathy. Furthermore, the subject may be a human, another mammal, or another suitable subject.

In certain embodiments, this disclosure provides methods for treating a subject having a cardiomyopathy comprising administering to the subject a therapeutically effective amount of a pharmaceutical composition. In various embodiments, the pharmaceutical composition may comprise a fusion protein including a tafazzin peptide and a cellular permeability peptide. Additionally, the fusion protein may be isolated and/or purified. The therapeutically effective amount of the pharmaceutical composition may also comprise a pharmaceutically acceptable carrier.

In some embodiments, the fusion protein may comprise a tafazzin peptide that is coupled to the cellular permeability peptide by a polypeptide linker. The tafazzin peptide may be selected from at least one of SEQ ID NO:1 (human TAZ wild type full length (NCBI RefSeq no. NP 000107.1)), SEQ ID NO:2 (human TAZ wild type lacking exon 5 (NCBI RefSeq no. NP 851828.1)), SEQ ID NO:3 (mouse TAZ wild type (NCBI RefSeq no. NP 852657.1)), SEQ ID NO:4 (human-mouse chimeric protein), and SEQ ID NO:5 (mouse-human chimeric protein).

In some embodiments, the fusion protein comprising the tafazzin peptide and the cellular permeability peptide may comprise a tafazzin peptide that is at least eighty percent identical to at least one of SEQ ID NO:1, SEQ ID NO:2, SEQ ID NO:3, SEQ ID NO:4, and SEQ ID NO:5. In other embodiments, the fusion protein comprising the tafazzin peptide and the cellular permeability peptide may comprise a peptide that is at least sixty percent identical to at least one of SEQ ID NO:1, SEQ ID NO:2, SEQ ID NO:3, SEQ ID NO:4, and SEQ ID NO:5. In yet other embodiments, the fusion protein comprising the tafazzin peptide and the cellular permeability peptide may comprise a peptide that is at least forty percent identical to at least one of SEQ ID NO:1, SEQ ID NO:2, SEQ ID NO:3, SEQ ID NO:4, and SEQ ID NO:5. In still other embodiments, the fusion protein comprising the tafazzin peptide and the cellular permeability peptide may comprise a peptide that is at least twenty percent identical to at least one of SEQ ID NO:1, SEQ ID NO:2, SEQ ID NO:3, SEQ ID NO:4, and SEQ ID NO:5.

In certain embodiments, the cellular permeability peptide may comprise an antennapedia permeability peptide. For example, the fusion protein may comprise a tafazzin peptide and an antennapedia permeability peptide. The fusion protein may also comprise a tafazzin peptide coupled to an antennapedia permeability peptide. In some embodiments, the antennapedia permeability peptide may comprise SEQ ID NO:6 (Antennapedia permeability peptide).

In various embodiments, the antennapedia permeability peptide may comprise a peptide that is at least eighty percent identical to SEQ ID NO:6. In other embodiments, the antennapedia permeability peptide may comprise a peptide that is at least sixty percent identical to SEQ ID NO:6. In yet other embodiments, the antennapedia permeability peptide may comprise a peptide that is at least forty percent identical to SEQ ID NO:6. In still other embodiments, the antennapedia permeability peptide may comprise a peptide that is at least twenty percent identical to SEQ ID NO:6.

In some other embodiments, the cellular permeability peptide may comprise an HIV Tat permeability peptide. For example, the fusion protein may comprise a tafazzin peptide and an HIV Tat permeability peptide. The fusion protein may also comprise a tafazzin peptide coupled to an HIV Tat permeability peptide. In some embodiments, the HIV Tat permeability peptide may comprise SEQ ID NO:7 (HIV Tat permeability peptide).

In certain embodiments, the HIV Tat permeability peptide may comprise a peptide that is at least eighty percent identical to SEQ ID NO:7. In other embodiments, the HIV Tat permeability peptide may comprise a peptide that is at least sixty percent identical to SEQ ID NO:7. In yet other embodiments, the HIV Tat permeability peptide may comprise a peptide that is at least forty percent identical to SEQ ID NO:7. In still other embodiments, the HIV Tat permeability peptide may comprise a peptide that is at least twenty percent identical to SEQ ID NO:7.

In some other embodiments, the cellular permeability peptide may comprise a cardiac targeting peptide (CTP). For example, the fusion protein may comprise a tafazzin peptide and a CTP. The fusion protein may also comprise a tafazzin peptide coupled to a CTP. In some embodiments, the CTP may comprise SEQ ID NO:8 (Cardiac Targeting Peptide (CTP)).

In certain embodiments, the CTP may comprise a peptide that is at least eighty percent identical to SEQ ID NO:8. In other embodiments, the CTP may comprise a peptide that is at least sixty percent identical to SEQ ID NO:8. In yet other embodiments, the CTP may comprise a peptide that is at least forty percent identical to SEQ ID NO:8. In still other embodiments, the CTP may comprise a peptide that is at least twenty percent identical to SEQ ID NO:8.

In some other embodiments, the cellular permeability peptide may comprise a Kaposi FGF4-permeability peptide. For example, the fusion protein may comprise a tafazzin peptide and a Kaposi FGF4-permeability peptide. The fusion protein may also comprise a tafazzin peptide coupled to a Kaposi FGF4-permeability peptide. In some embodiments, the Kaposi FGF4-permeability peptide may comprise SEQ ID NO:9 (Kaposi FGF4-derived peptide).

In various embodiments, the Kaposi FGF4-permeability peptide may comprise a peptide that is at least eighty percent identical to SEQ ID NO:9. In other embodiments, the Kaposi FGF4-permeability peptide may comprise a peptide that is at least sixty percent identical to SEQ ID NO:9. In yet other embodiments, the Kaposi FGF4-permeability peptide may comprise a peptide that is at least forty percent identical to SEQ ID NO:9. In still other embodiments, the Kaposi FGF4-permeability peptide may comprise a peptide that is at least twenty percent identical to SEQ ID NO:9.

In some embodiments, the tafazzin peptide may be coupled to the cellular permeability peptide (e.g., an antennapedia permeability peptide, an HIV Tat permeability peptide, a CTP, or a Kaposi FGF4-permeability peptide) by a polypeptide linker. In certain embodiments, the tafazzin peptide coupled to the cellular permeability peptide by the polypeptide linker may comprise a peptide selected from the group consisting of SEQ ID NO:10 (mouse TAZ-Antp), SEQ ID NO:11 (human TAZ-Antp), SEQ ID NO:12 (mouse TAZ-CTP), and SEQ ID NO:13 (human TAZ-CTP).

In certain embodiments, the tafazzin peptide coupled to the cellular permeability peptide by a polypeptide linker may comprise a peptide that is at least eighty percent identical to at least one of SEQ ID NO:10, SEQ ID NO:11, SEQ ID NO:12, and SEQ ID NO:13. In other embodiments, the tafazzin peptide coupled to the cellular permeability peptide by a polypeptide linker may comprise a peptide that is at least sixty percent identical to at least one of SEQ ID NO:10, SEQ ID NO:11, SEQ ID NO:12, and SEQ ID NO:13. In yet other embodiments, the tafazzin peptide coupled to the cellular permeability peptide by a polypeptide linker may comprise a peptide that is at least forty percent identical to at least one of SEQ ID NO:10, SEQ ID NO:11, SEQ ID NO:12, and SEQ ID NO:13. In still other embodiments, the tafazzin peptide coupled to the cellular permeability peptide by a polypeptide linker may comprise a peptide that is at least twenty percent identical to at least one of SEQ ID NO:10, SEQ ID NO:11, SEQ ID NO:12 and SEQ ID NO:13.

In various embodiments, the methods for treating a subject having a cardiomyopathy may comprise administering to the subject an effective amount of a pharmaceutical composition to reduce a pathological effect or symptom of the cardiomyopathy. As described above, the pharmaceutical composition may comprise a fusion protein including a tafazzin peptide and a cellular permeability peptide. The pharmaceutical composition may further comprise a pharmaceutically acceptable carrier. The methods for treating a subject having a cardiomyopathy may further comprise identifying the subject having the cardiomyopathy.

In some embodiments, the cardiomyopathy may be selected from at least one of chemotherapy-induced cardiomyopathy, diabetic cardiomyopathy, dilated cardiomyopathy, hypertensive cardiomyopathy, hypertrophic cardiomyopathy, ischemic cardiomyopathy, and/or noncompaction cardiomyopathy. In certain embodiments, the cardiomyopathy may be associated with a tafazzin gene (TAZ) mutation. In certain other embodiments, the chemotherapy-induced cardiomyopathy, diabetic cardiomyopathy, dilated cardiomyopathy, hypertensive cardiomyopathy, hypertrophic cardiomyopathy, ischemic cardiomyopathy, and/or noncompaction cardiomyopathy may be associated with a tafazzin gene (TAZ) mutation.

In certain embodiments, the cardiomyopathy may not be associated with a tafazzin gene (TAZ) mutation. Nevertheless, a subject having a cardiomyopathy (e.g., chemotherapy-induced cardiomyopathy, diabetic cardiomyopathy, dilated cardiomyopathy, hypertensive cardiomyopathy, hypertrophic cardiomyopathy, ischemic cardiomyopathy, and/or noncompaction cardiomyopathy) that is not associated with a tafazzin gene (TAZ) mutation may benefit from treatment with a pharmaceutical composition comprising a fusion protein including a tafazzin peptide and a cellular permeability peptide. The pharmaceutical composition may further comprise a pharmaceutically acceptable carrier.

In various embodiments, the pharmaceutical composition may reduce or be configured to reduce a pathological effect or symptom of the cardiomyopathy. The pathological effect or symptom of the cardiomyopathy may be selected from, but not limited to, at least one of dyspnea, heart enlargement, cardiac fibrosis, pulmonary congestion, peripheral edema, irregular heart rate, hypotension, and/or fatigue.

Another aspect of the disclosure relates to methods of prophylactically treating, or methods for prophylactic treatment of, a subject or patient at risk of developing a cardiomyopathy. The cardiomyopathy may be selected from at least one of chemotherapy-induced cardiomyopathy, diabetic cardiomyopathy, dilated cardiomyopathy, hypertensive cardiomyopathy, hypertrophic cardiomyopathy, ischemic cardiomyopathy, and/or noncompaction cardiomyopathy. For example, the methods may comprise treating a subject at risk of developing dilated cardiomyopathy. Furthermore, the subject may be a human, another mammal, or another suitable subject.

In certain embodiments, this disclosure provides methods for prophylactically treating a subject at risk of developing a cardiomyopathy comprising administering to the subject a therapeutically effective amount of a pharmaceutical composition. In various embodiments, the pharmaceutical composition may comprise a fusion protein including a tafazzin peptide and a cellular permeability peptide. Additionally, the fusion protein may be isolated and/or purified. The therapeutically effective amount of the pharmaceutical composition may also comprise a pharmaceutically acceptable carrier.

As discussed above regarding methods of treating a subject having a cardiomyopathy, the fusion protein may comprise a tafazzin peptide that is coupled to the cellular permeability peptide by a polypeptide linker. In various embodiments, the tafazzin peptide may be selected from at least one of SEQ ID NO:1, SEQ ID NO:2, SEQ ID NO:3, SEQ ID NO:4, and SEQ ID NO:5. In various other embodiments, the tafazzin peptide may comprise a peptide that is at least eighty percent, at least sixty percent, at least forty percent, or at least twenty percent identical to at least one of SEQ ID NO:1, SEQ ID NO:2, SEQ ID NO:3, SEQ ID NO:4, and SEQ ID NO:5.

Additionally, as discussed above regarding methods of treating a subject having a cardiomyopathy, the fusion protein may comprise a cellular permeability peptide selected from at least one of a cardiac targeting peptide, an antennapedia permeability peptide, an HIV Tat permeability peptide, and/or a Kaposi FGF4-permeability peptide.

In some embodiments, as described above, the tafazzin peptide may be coupled to the cellular permeability peptide (e.g., an antennapedia permeability peptide, an HIV Tat permeability peptide, a CTP, or a Kaposi FGF4-permeability peptide) by a polypeptide linker. In certain embodiments, the tafazzin peptide coupled to the cellular permeability peptide by the polypeptide linker may comprise a peptide selected from the group consisting of SEQ ID NO:10, SEQ ID NO:11, SEQ ID NO:12, and SEQ ID NO:13.

In certain embodiments, the tafazzin peptide coupled to the cellular permeability peptide by a polypeptide linker may comprise a peptide that is at least eighty percent, at least sixty percent, at least forty percent, or at least twenty percent identical to at least one of SEQ ID NO:10, SEQ ID NO:11, SEQ ID NO:12, and SEQ ID NO:13.

In various embodiments, the methods for prophylactically treating a subject at risk of developing a cardiomyopathy may comprise administering to the subject an effective amount of a pharmaceutical composition to reduce a risk of developing a pathological effect or symptom of the cardiomyopathy. For example, the pharmaceutical composition may reduce or be configured to reduce a risk of developing a pathological effect or symptom of a cardiomyopathy. The pathological effect or symptom of the cardiomyopathy may be selected from, but not limited to, at least one of dyspnea, heart enlargement, cardiac fibrosis, pulmonary congestion, peripheral edema, irregular heart rate, hypotension, and/or fatigue. The methods for treating a subject at risk of developing a cardiomyopathy may further comprise identifying the subject at risk of developing the cardiomyopathy. In some embodiments, the subject at risk of developing the cardiomyopathy may have a tafazzin gene (TAZ) mutation.

EXAMPLES

The following examples are illustrative of disclosed methods and compositions. In light of this disclosure, those of skill in the art will recognize that variations of these examples and other examples of the disclosed methods and compositions would be possible without undue experimentation.

Figure 1B:
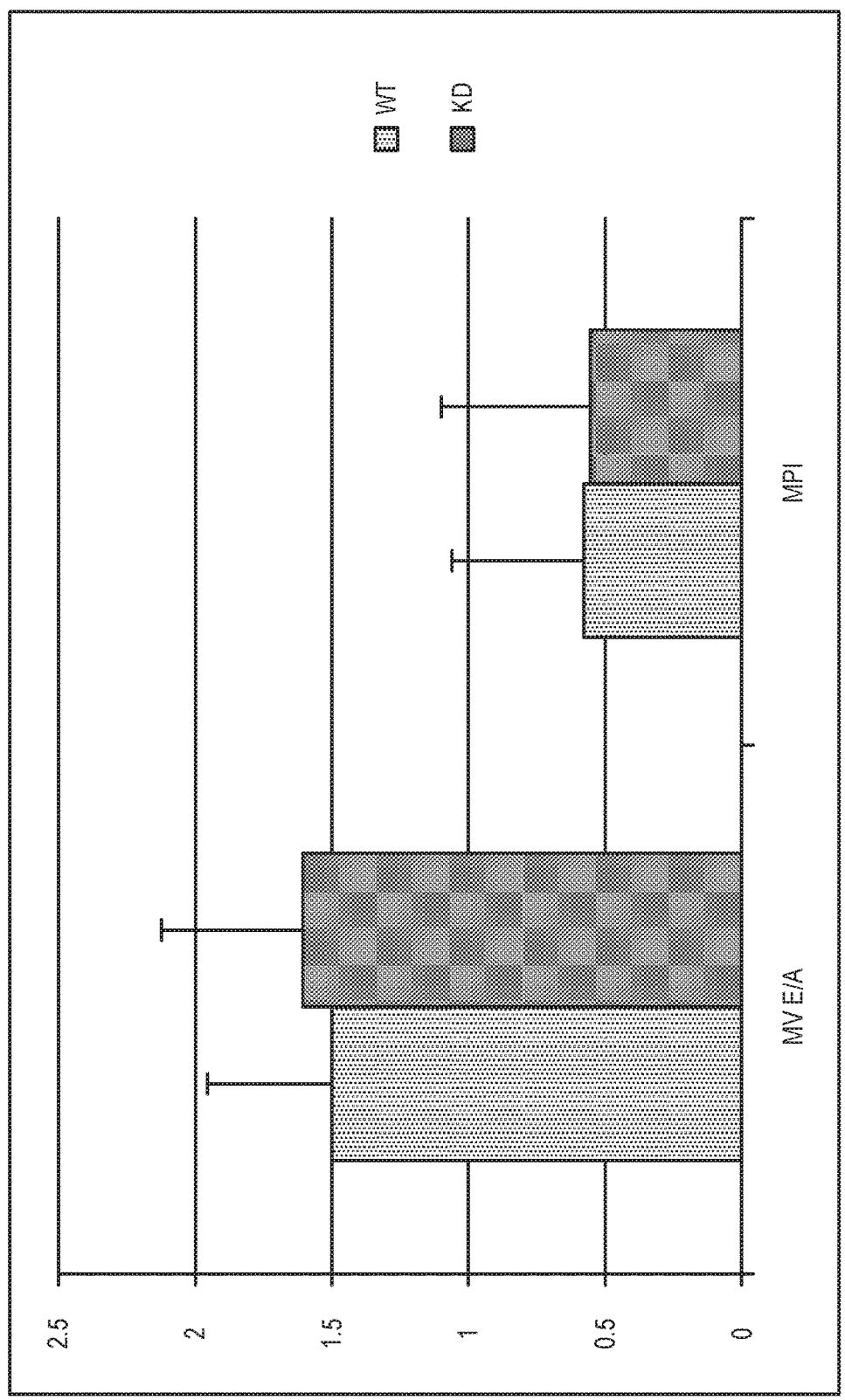
FIG. 1B is a graph depicting E/A ratio (MV E/A) and myocardial performance index (MPI) in wild-type (WT) and TAZ-knockdown (KD) mice at 8 weeks of age. As depicted, TAZ-KD mice show normal E/A ratio and MPI at 8 weeks of age.

Example 1—Mice Deficient in TAZ Have Normal Ventricular Function at Baseline and Isolated Myocytes Have Normal Fractional Shortening and Relaxation Time Doxycycline-inducible TAZ-knockdown mice were obtained from THE JACKSON LABORATORY™ and females were fed with doxycycline chow (625 mg/kg) prior to mating so that offspring would have induction of shRNA directed against TAZ from the time of conception. These offspring were then raised to the age of 8 weeks and baseline echocardiography was performed. As shown in FIGS. 1A and 1B, substantially no difference is observed in baseline fractional shortening (% FS), ejection fraction (% EF), E/A ratio (MV E/A), or myocardial performance index (MPI).

Figure 2:
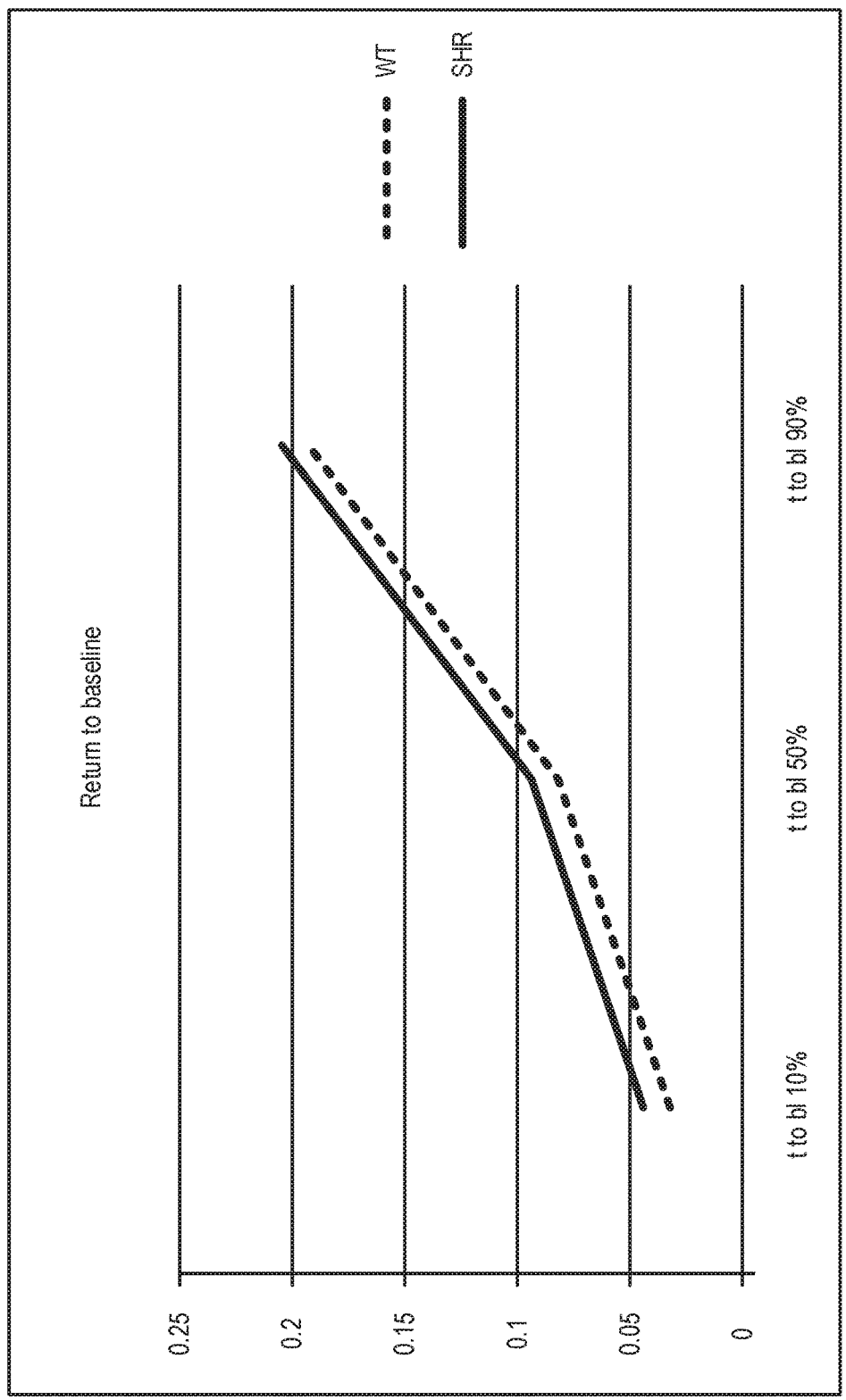
FIG. 2 is a graph depicting relaxation in adult cardiomyocytes isolated from 2-month old wild-type (WT) and TAZ-knockdown (SHR) mice. As depicted, adult cardiomyocytes isolated from 2-month-old wild-type and TAZ-knockdown mice show nearly or substantially identical relaxation.

To determine whether TAZ-KD hearts exhibit any defects at the myocyte level, adult cardiac myocytes were isolated from 8-week-old TAZ-KD mice and fractional shortening, calcium transient, and diastolic relaxation were assessed using an IONOPTIX™ myocyte calcium and contractility system (see Liu Y, et al., Am J Physiol Heart Circ Physiol, 2012; 302(9):H1860-70). As shown in Table 1 (see below), adult myocytes from 2-month-old TAZ-KD mice were longer, but had similar fractional shortening, sarcomere length, and calcium transients when compared with WT myocytes. FIG. 2 illustrates that the kinetics of relaxation are substantially identical in wild-type (WT) and TAZ-KD (SHR) cells, indicating that diastolic relaxation is not impaired at the cellular level.

TABLE 1

Adult Cardiomyocyte IONOPTIX™ Data from WT and TAZ-KD Mice

| | Cell Length | | | Sarcomere Length | | Fura-2 | |
|---|---|---|---|---|---|---|---|
| | Baseline | Peak | PS | Baseline | Peak | Baseline | Peak |
| WT | 123.944 | 116.776 | 0.058 | 1.706 | 1.565 | 1.268 | 1.384 |
| KD | 133.213 | 127.473 | 0.043 | 1.743 | 1.640 | 1.244 | 1.325 |
| p-value | 0.009 | 0.064 | 0.486 | 0.659 | 0.641 | 0.829 | 0.809 |

Example 2—Recombinant Tafazzins Tethered to Cell Penetrating Peptides Enter Cells and Localize to Mitochondria To develop a potential treatment for TAZ deficiency, recombinant tafazzin proteins were engineered containing a short peptide at the C-terminus, derived from either the *Drosophila* antennapedia protein (Antp), which has been shown to promote uptake of proteins into cells (see Rapoport M, et al., Mol Ther, 2008; 16(4):691-7; Schwarze S R, et al., Trends Cell Biol, 2000; 10(7):290-5; and Zhou H, et al., Cell Stem Cell, 2009; 4(5):381-4) or a cardiac targeting peptide (CTP) (see Zahid M, et al., PLoS One, 2010; 5(8):e12252). The antennapedia peptide has been shown to facilitate entry of proteins into cells through a mechanism that may involve interactions with highly cationic basic residues (see Schwarze S R, et al., Trends Cell Biol, 2000; 10(7):290-5).

Figure 3A:
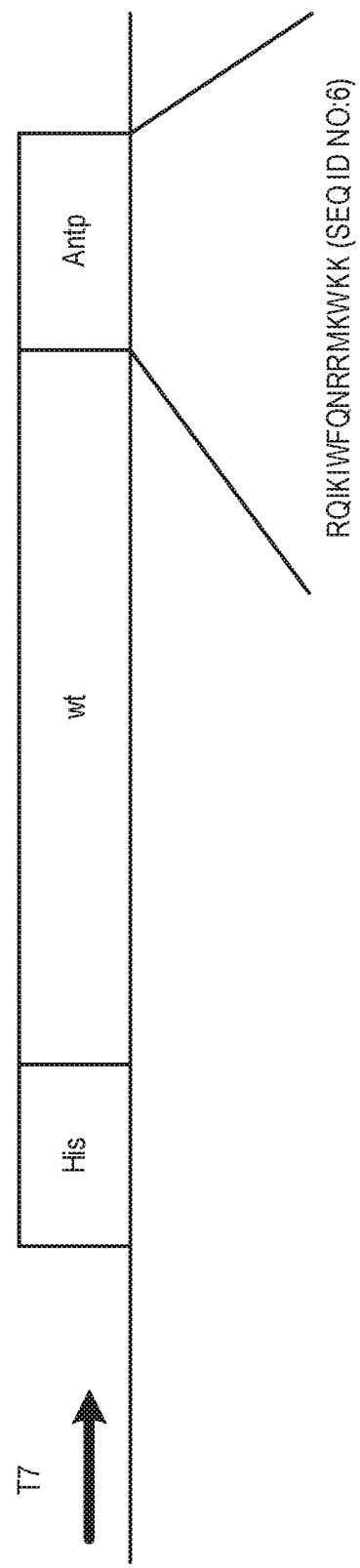
FIG. 3A is a tafazzin recombinant protein construct comprising a His tag in the N-terminus and an antennapedia (Antp) tag in the C-terminus.
Figure 3B:
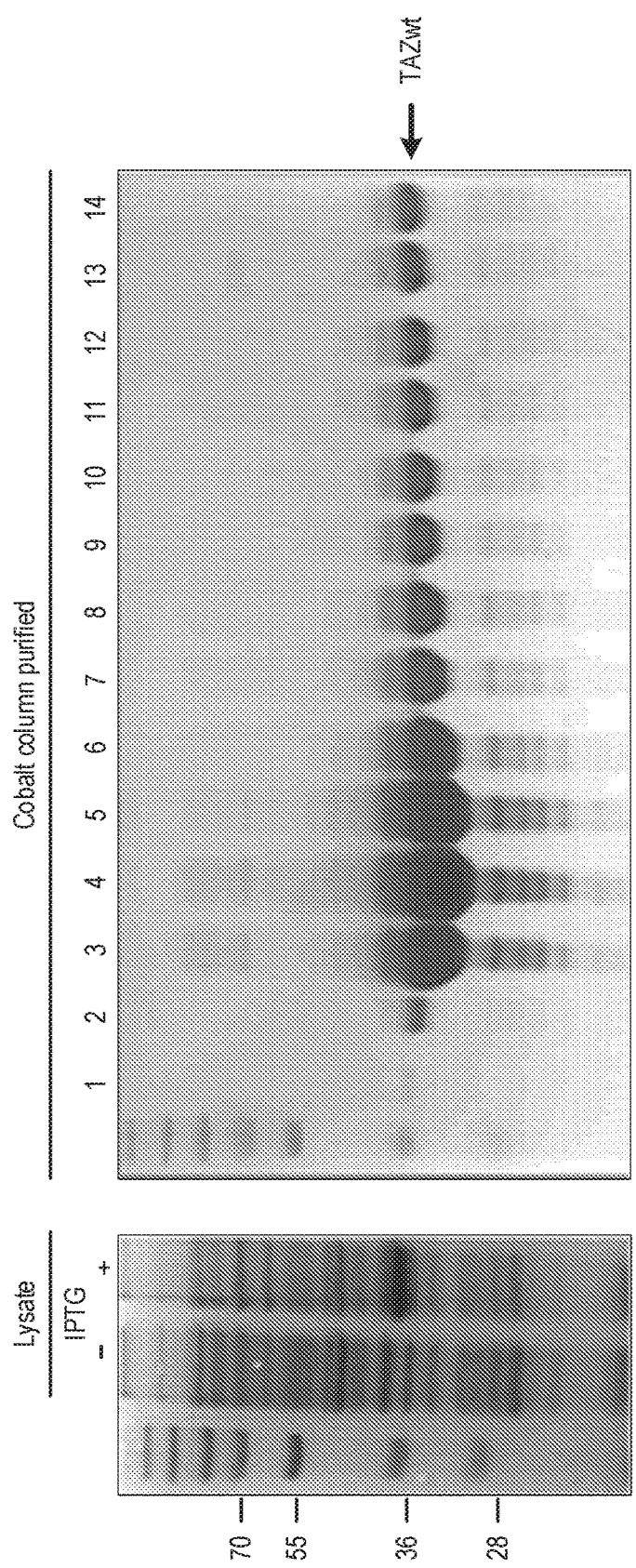
FIG. 3B is an SDS-PAGE of tafazzin (TAZ) wild-type (WT) mouse protein (comprising Antp at the C-terminus) depicting induction in BL21(DE3) cells and purification. Bacterial cells were pre-cultured for 2 hours and subsequently induced with 0.5 mM IPTG for 2 hours. The left panel gel shows pre-(lane 2) and post-(lane 3) induction bacterial lysates. The cells were then lysed and His-tagged tafazzin was purified using a Cobalt (Co) column, as shown in the right panel.
Figure 4:
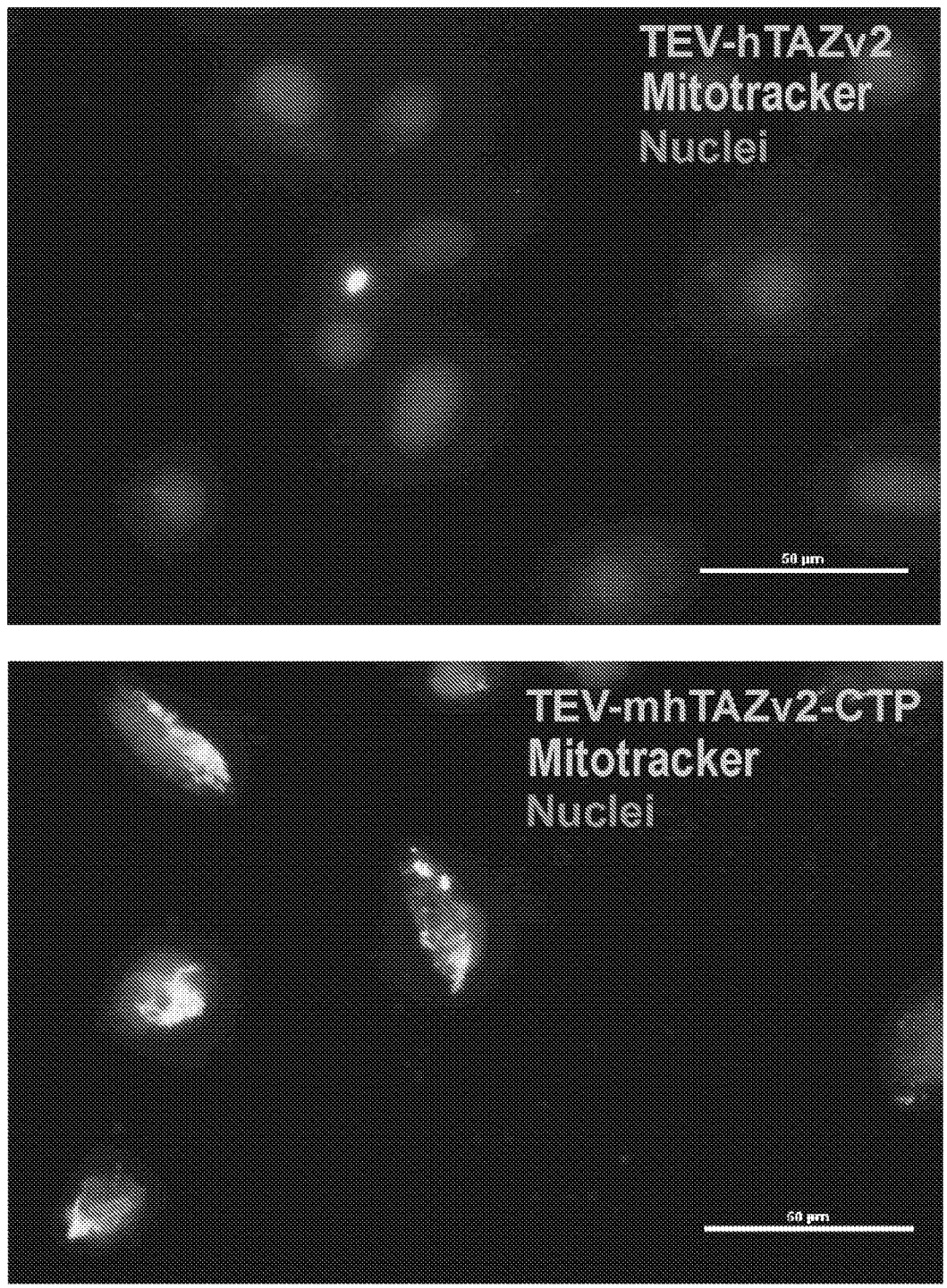
FIG. 4 is a series of micrographs depicting that recombinant tafazzin tagged with cardiac targeting peptide (CTP) localizes to mitochondria. H9c2 myoblasts were treated with untagged TAZ (top panel) or TAZ-CTP (bottom panel). Protein uptake was detected by immunofluorescence and mitochondrial colocalization was detected by overlap with MITOTRACKER® dye.

Recombinant tafazzin was induced and purified using *E. coli* (see FIGS. 3A and 3B) and the ability of the recombinant protein to enter H9c2 myoblasts was tested. CTP-tagged TAZ protein successfully entered the cells and colocalized with mitochondria, while TAZ lacking CTP did not enter the cell (see FIG. 4). The association of TAZ-Antp with the mitochondrial fraction after treatment was also analyzed and TAZ-Antp co-purifies with mitochondria.

Figure 5:
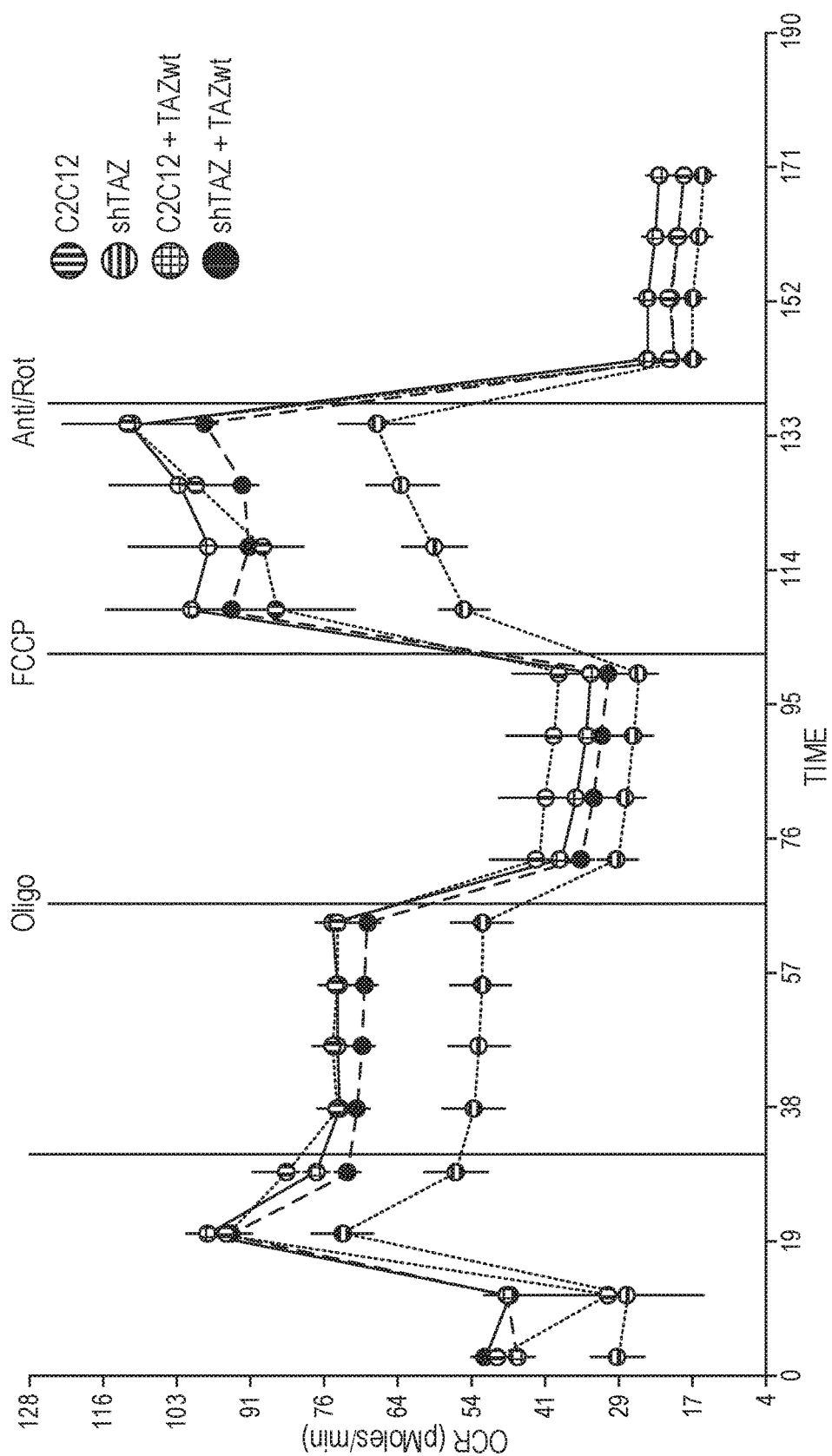
FIG. 5 is a graph depicting that recombinant tafazzin tagged with Antp rescues defective mitochondrial respiration in TAZ-KD cells. The oxygen consumption rate in C2C12 WT or TAZ-KD cells was measured after treatment with vehicle or TAZ-Antp. Both basal respiration (before oligomycin treatment) and maximal respiration (after FCCP administration) were reduced in TAZ-KD cells compared to WT. After treatment with TAZ-Antp, respiration in TAZ-KD was restored to WT levels.

Example 3—Recombinant Tafazzin Rescues Defective Mitochondrial Respiration in Tafazzin-Deficient Cells To determine whether the recombinant protein can rescue defective mitochondrial respiration, mitochondrial respiration measurements were conducted using a SEAHORSE BIOSCIENCE™ Extracellular Flux Analyzer to determine the oxygen consumption rate in both wild type and C2C12 myoblasts in which TAZ is knocked down by a lentiviral shRNA construct and in which palmitate is used as a substrate. Measurements were conducted both at baseline and under mitochondrial stress conditions using oligomycin, an ATP synthase inhibitor; FCCP, an electron transport chain accelerator; and rotenone, which completely blocks mitochondrial respiration. FIG. 5 shows the respiration measurements of wild type C2C12 myoblasts, as well as TAZ-KD C2C12 cells, with or without treatment with wild type tafazzin protein tagged with Antp peptide.

TAZ-KD cells show a marked decrease in baseline and maximal oxygen consumption as compared to the wild type cells; this is consistent with data from Barth syndrome patient-derived fibroblasts (see Houtkooper R H, et al., Biochim Biophys Acta, 2009; 1788(10):2003-14), and lymphocytes and cardiomyocytes isolated from a Barth syndrome mouse model. While wild type cells treated with tafazzin show only a slight trend in increase of oxygen consumption during maximal respiration, the TAZ-deficient cells are rescued to essentially wild-type oxygen consumption levels. Without being bound by any particular theory, these results may indicate that the protein is able to reach the mitochondria where it is enzymatically active and able to restore respiration. A similar analysis done in primary neonatal cardiomyocytes isolated from TAZ-KD mice comparing TAZ-Antp and TAZ-CTP and using glucose as a substrate showed that both proteins could augment respiration in both TAZ-KD and WT cells, with TAZ-CTP giving slightly better results in WT cells.

Figure 6:
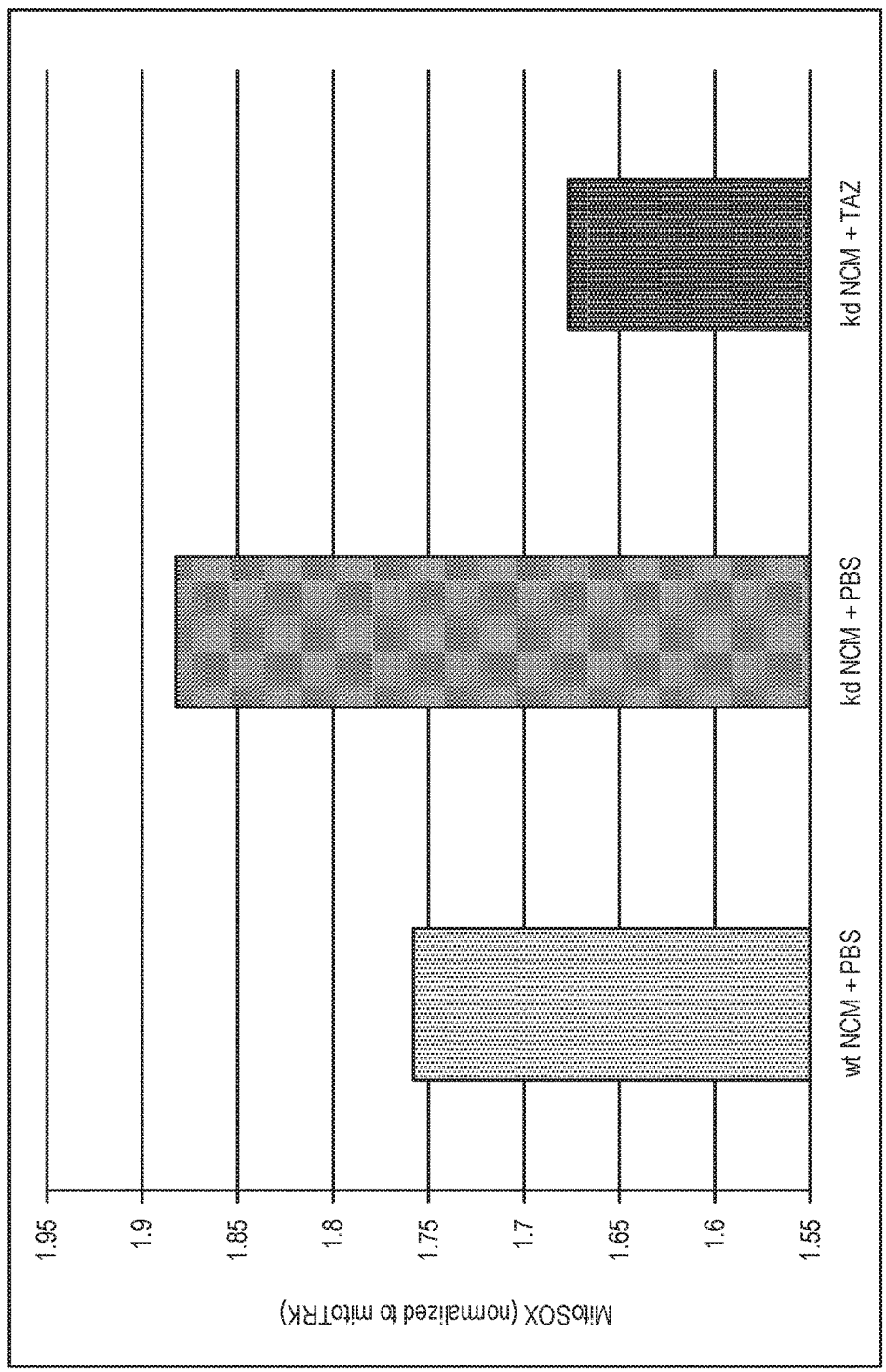
FIG. 6 is a graph depicting ROS levels in WT and TAZ-KD neonatal cardiomyocytes (NCM) at baseline and after TAZ-Antp treatment.

Example 4—Tafazzin-Deficient Neonatal Cardiomyocytes Demonstrate Increased Amounts of ROS That can be Suppressed by Recombinant Tafazzin To determine whether tafazzin deficiency leads to increased ROS generation in cardiomyocytes, neonatal cardiomyocytes were isolated from TAZ-KD and WT littermates and ROS levels were measured with MITOSOX™ Red, a mitochondrial superoxide indicator, and total mitochondria were measured with MITOTRACKER® Green FM, a green-fluorescent mitochondrial stain, staining according to the manufacturer's instructions (LIFE TECHNOLOGIES™). As shown in FIG. 6, ROS levels normalized to total mitochondria were increased in TAZ-KD cells. Treatment with TAZ-Antp suppressed ROS levels to levels comparable to wild-type cells.

Example 5—Recombinant Tafazzin can be Delivered Directly to the Heart

Figure 7:
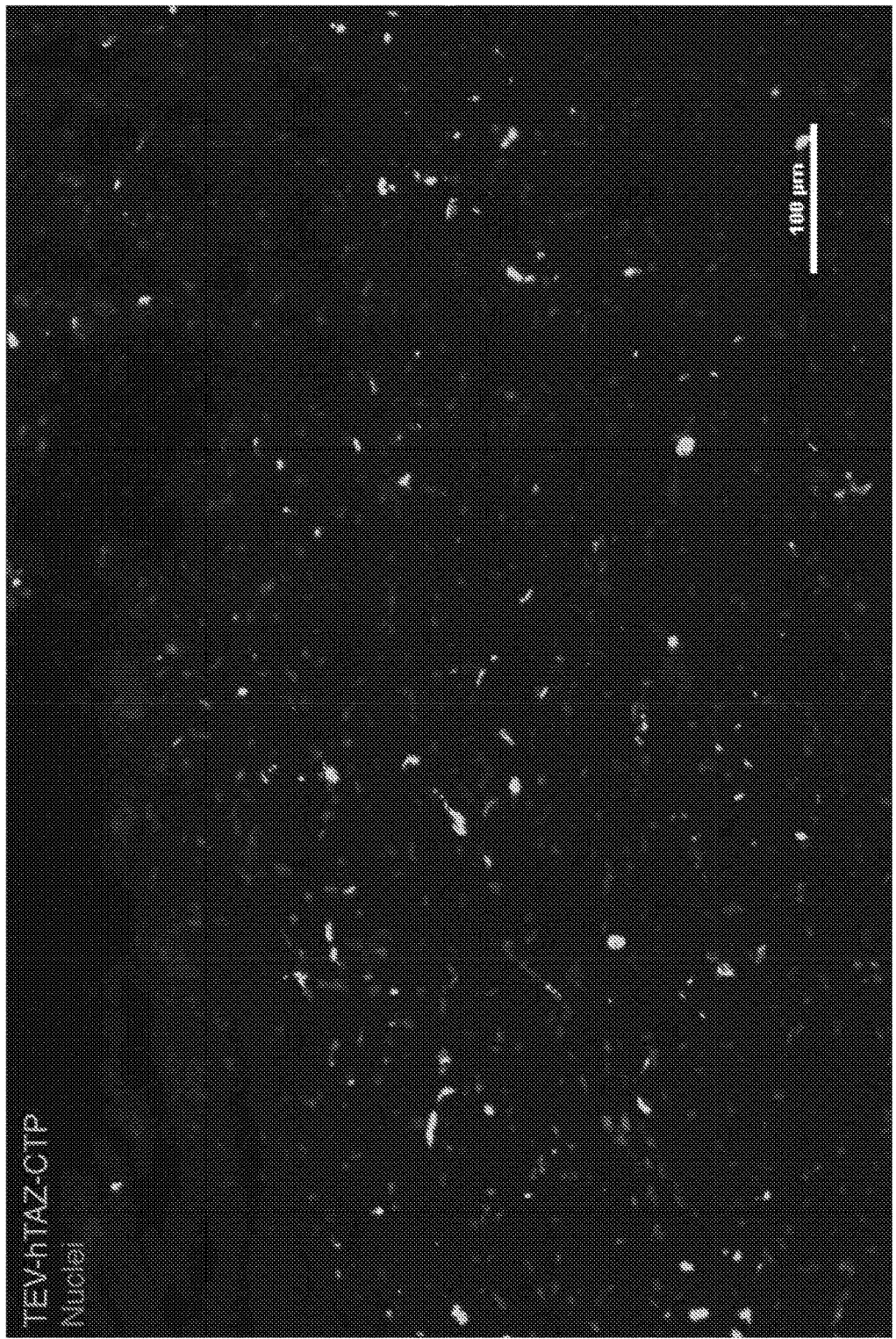
FIG. 7 is a micrograph depicting TAZ-CTP uptake into the myocardium. As depicted, coronary infusion of TAZ-CTP promotes uptake into the myocardium.
Figure 8A:
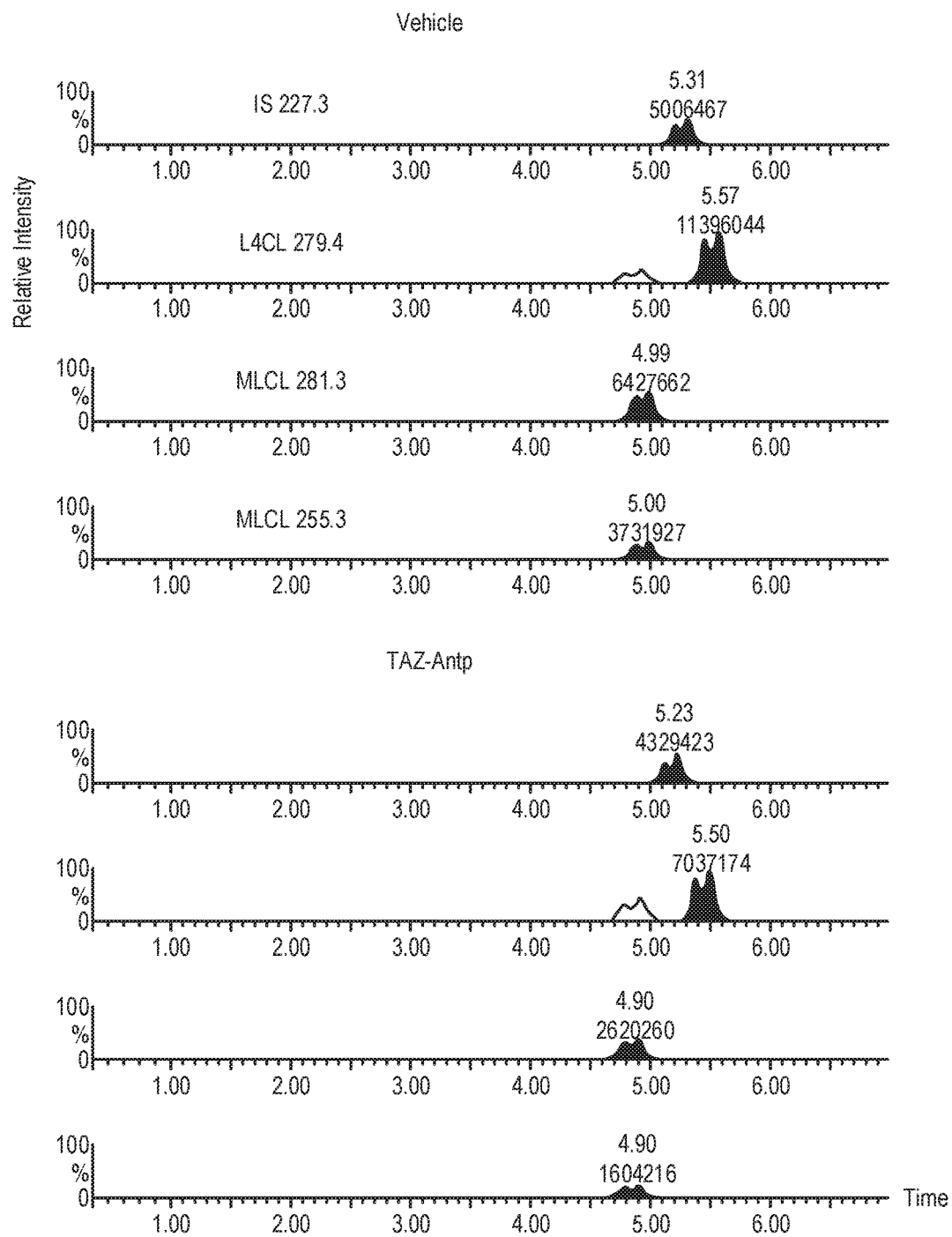
FIG. 8A is a series of multiple reaction monitoring (MRM) chromatograms for monolysocardiolipin (MLCL, sum of m/z 582.9→m/z 281.3 and m/z 582.9→m/z 255.3) and tetralinoleoyl cardiolipin (L4CL, m/z 723.8→m/z 279.4) in heart tissue from TAZ knockdown mice treated with either vehicle control or TAZ-Antp.
Figure 8B:
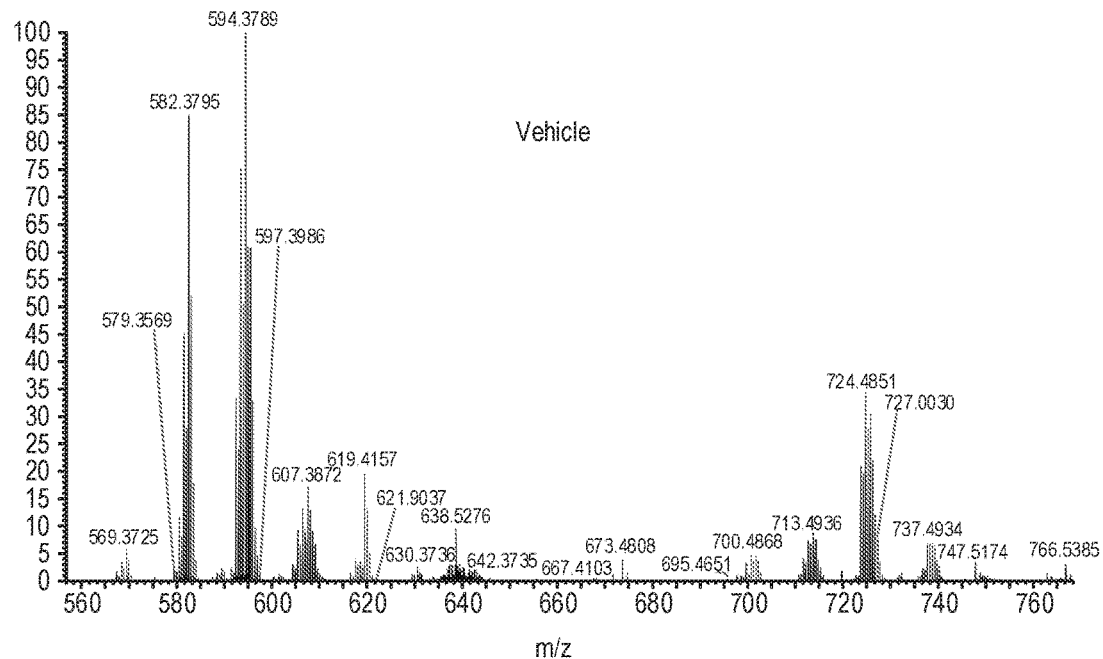
FIG. 8B shows LC-MS spectra of cardiolipin from TAZ knockdown mouse hearts treated with either vehicle control or TAZ-Antp.
Figure 8B:
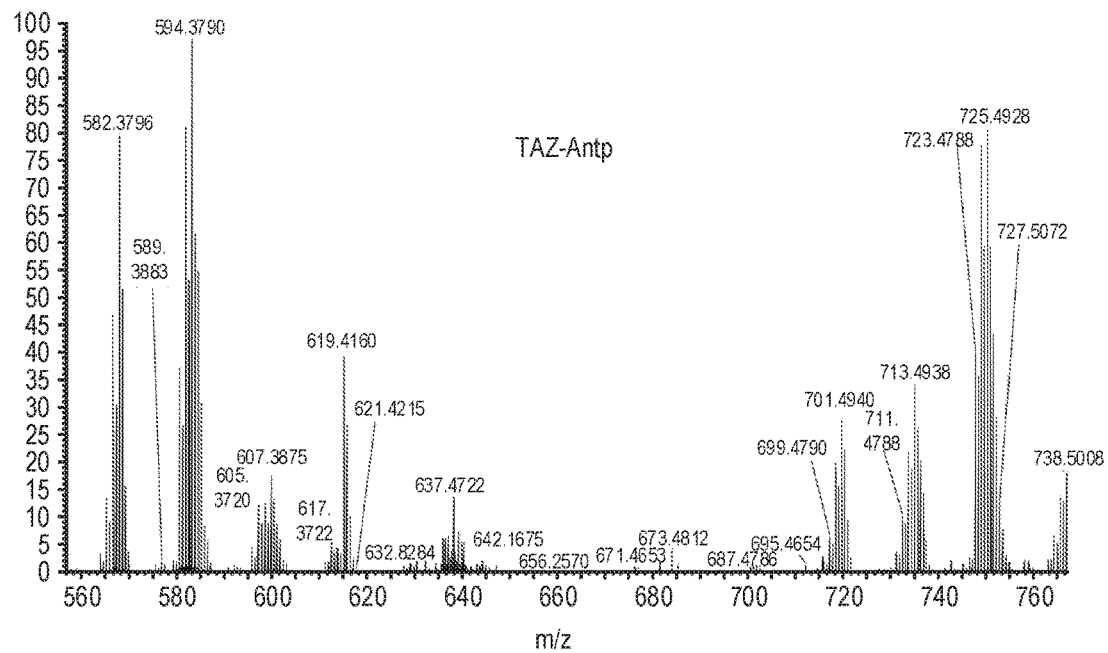
Figure 8C:
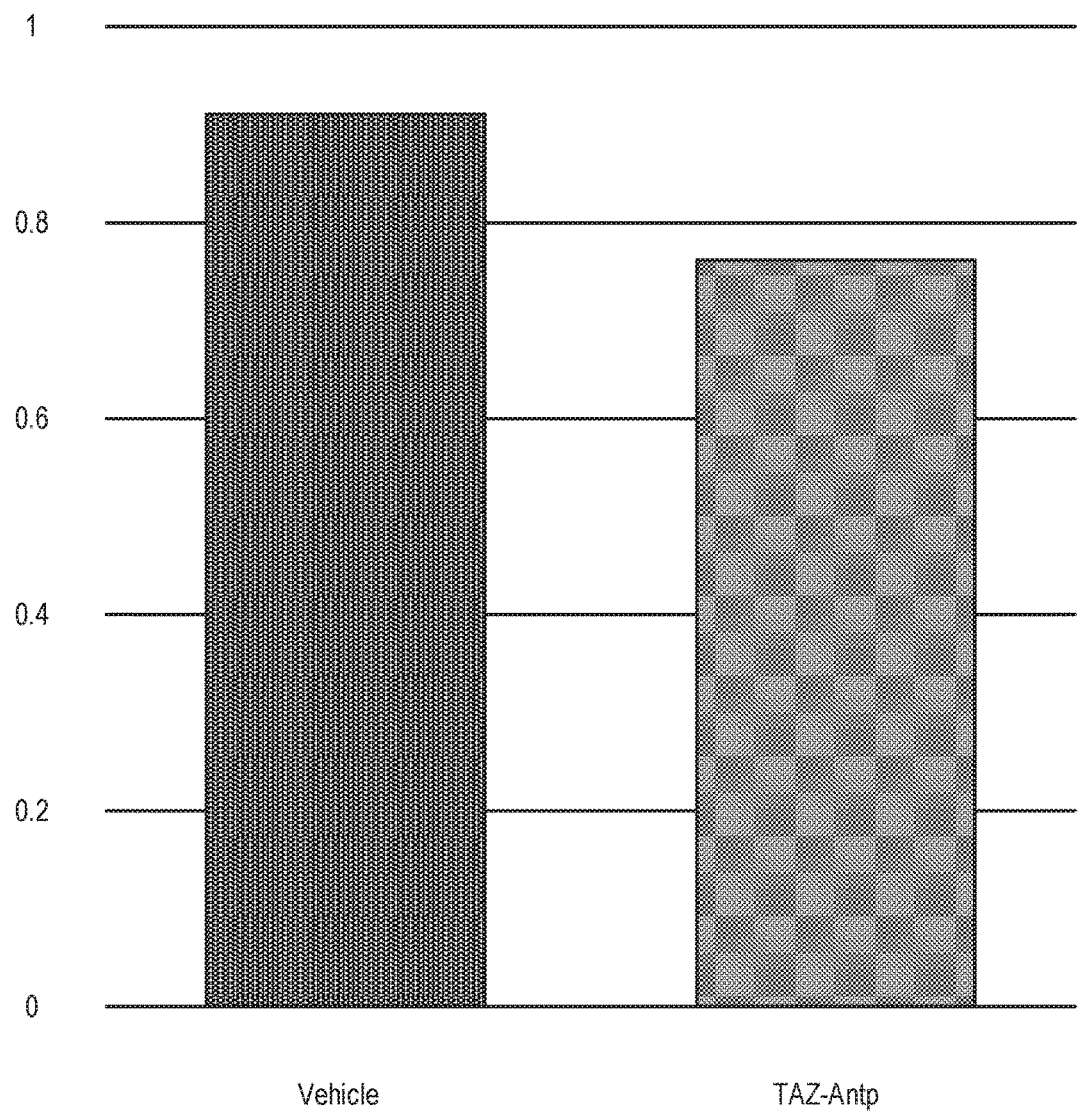
FIG. 8C is a graph depicting the MLCL/L4CL ratio in hearts from TAZ-Antp and vehicle control treated TAZ knockdown mice.
Figure 8D:
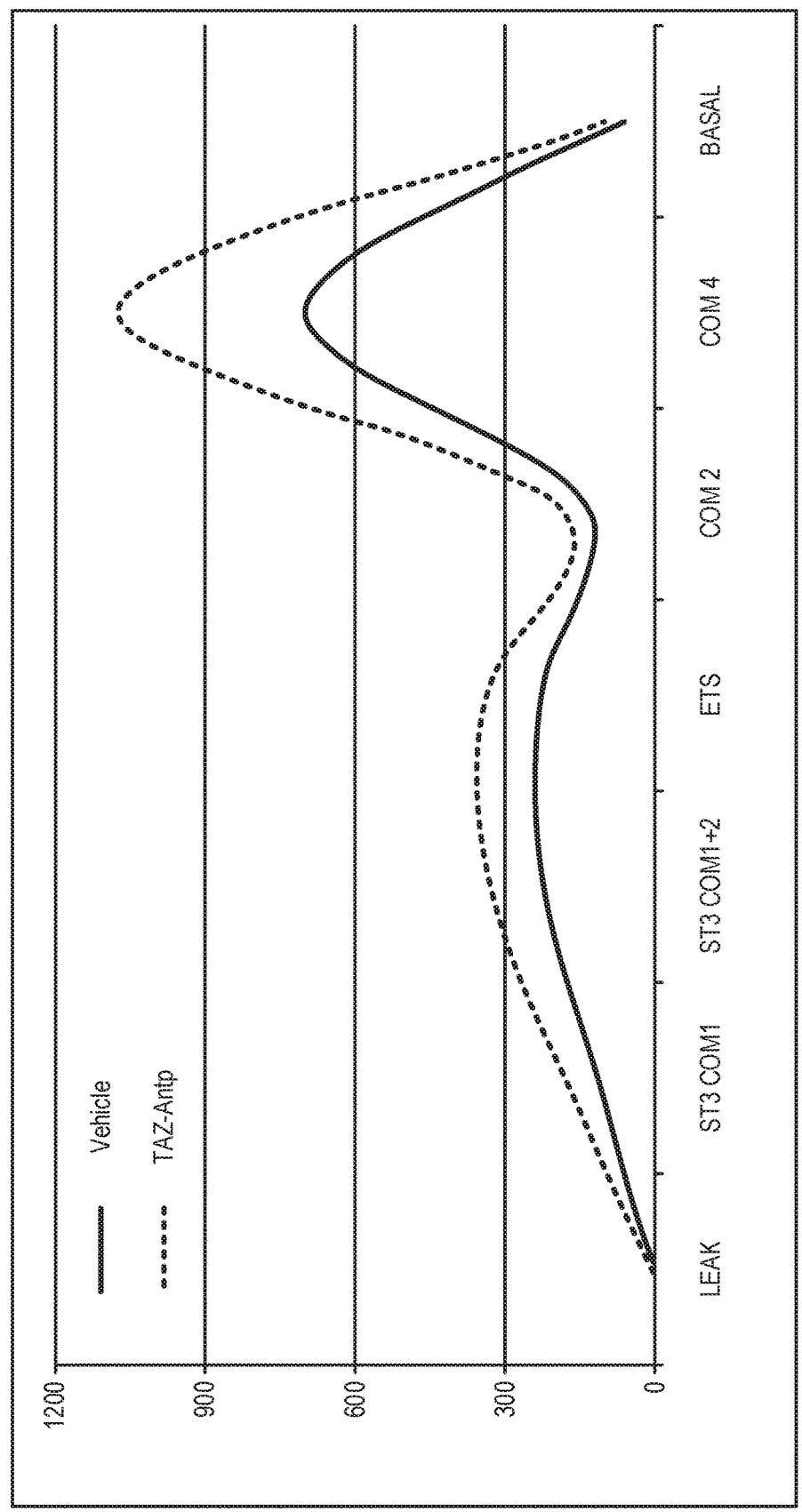
FIG. 8D is a graph depicting oxygen consumption rates in TAZ knockdown mouse hearts measured with a high resolution OXYGRAPH-2K™ respirometer after treatment with either TAZ-Antp or vehicle control.

As an early step in optimizing protein delivery to the heart, TAZ-CTP was also delivered via coronary artery perfusion, with about 5% of cells demonstrating uptake by immunofluorescence (see FIG. 7). These findings demonstrated the feasibility of delivering tafazzin to the heart to rescue defective mitochondrial respiration.

Example 6—Systemic Infusion of Recombinant Tafazzin Alters the MLCL:L4CL Ratio and Augments Mitochondrial Respiration in Tafazzin-Deficient Hearts To determine whether recombinant tafazzin can be administered systemically, alter the MLCL:L4CL ratio, and improve mitochondrial respiration in the tafazzin-deficient heart, TAZ-KD mice were injected with either 40 μg recombinant TAZ-Antp or vehicle retroorbitally every other day and the hearts were then harvested on day 8 for LC-MS or oxygraph measurements. Mitochondrial respiration was measured in an OROBOROS INSTRUMENTS™ oxygraph chamber (see Dai D F, et al., Circ Res 2011; 108(7):837-46 and N'Guessan B, et al., Mol Cell Biochem, 2004; 256-257 (1-2):267-80). Equal amounts of heart samples were homogenized immediately prior to respirometric measurements, and then added to measurement chambers. Leak respiration was measured prior to addition of any substrates. State 3, Complex I activity was measured after the addition of malate, pyruvate, and glutamate; state 3, Complex I and II activity was measured after the addition of ADP and cytochrome C; the electron transport system (ETS) was measured after the addition of CCCP; Complex II activity was measured after the addition of antimycin A; non-mitochondrial respiration was measured after the addition of rotenone and this value was subtracted from all other measurements; and Complex IV activity after the addition of ascorbate and tetramethyl phenylenediamine (TMPD) and basal respiration were measured after the addition of potassium cyanide and this value was subtracted from the Complex IV value. As shown in FIGS. 8A-8D, recombinant TAZ-Antp administered systemically shifted the MLCL:L4CL ratio and increased activity of all measured mitochondrial complexes in TAZ-KD heart tissue.

Example 7—TAZ-Deficient Neonatal Myocytes May Demonstrate Increased ROS Generation and Increased Susceptibility to Hypertrophy and Increased Apoptosis Without being bound by any particular theory, it is hypothesized that TAZ deficiency may lead to increased ROS generation and greater hypertrophy than wild type controls. Neonatal mouse cardiac myocytes can be isolated. Both adult and neonatal mouse cardiac myocytes can be successfully cultured, as discussed above (see also Xiang F, et al., Am J Physiol Heart Circ Physiol, 2006; 290(5):H1997-H2006). Neonatal cardiac myocytes can be harvested by a modification of the method of Springhorn and Claycomb (see Biochem J, 1989; 258(1):73-8). Hearts can be removed and trimmed of atria and vascular tissue, and the remaining ventricular tissue from each heart can be cut into several pieces. Tissue can be incubated in trypsin/EDTA (CAMBREX™ CC-5012, 0.25 mg/ml, 5 ml for 8-10 ventricles) with rotation at 4° C. for 30 minutes. Cells can be collected by centrifugation at 1800 rpm for 5 minutes, followed by removal of supernatant and resuspension in Dulbecco's modified Eagle Medium (DMEM; GIBCO™, Cat. No. 11995-065, with penicillin, streptomycin, and fungizone) supplemented with 20% fetal calf serum (FCS). Cells can subsequently be collected by centrifugation, resuspended in 4 ml of collagenase type II solution (1 mg/ml) in Hanks' balanced salt solution (HBSS), and then transferred to a P60 dish and placed at 37° C. Cells can then be pipetted every 10 minutes until dispersed (up to 30-40 minutes), then filtered with a 70 μm nylon cell strainer (FALCON™ 35-2350) on a 50 ml tube to remove tissue debris. Collagenase can be neutralized in the filtrate by the addition of DMEM, 20% FCS. Cells can be collected by centrifugation at 800 rpm for 5 minutes, resuspended in 10 ml of DMEM, 20% FCS, and incubated on a P100 dish at 37° C. for 1-2 hour(s) to remove fibroblasts. The non-adherent cells can be collected by centrifugation of the culture medium at 800 rpm for 5 minutes, resuspended in 10.5 ml of DMEM, 20% FCS, and the number of cells can be quantified by Coulter counting. Cells can be seeded onto fibronectin-coated dishes at a density of $1\times10^5$/well in a 24-well plate for hypertrophy assays and $3–5\times10^6$ cells onto a P60 plate for other purposes. 20 μM Ara-C can be included in the culture medium to inhibit proliferation of any contaminating fibroblasts.

Hypertrophy in cultured neonatal mouse cardiac myocytes can be induced and assessed. Neonatal cardiac myocytes can be isolated as described above. For hypertrophy assays, cells can be stimulated with media containing 20% serum or media without serum supplemented with 30 μM phenylephrine (with 2 μM timolol), 100 μM angiotensin II, or 1 μM isoproterenol. Protein can be harvested at 0, 1, 3, 15, and 60 minutes after stimulation for analysis of signaling responses by western blotting. Some cells can be cultured up to 48 hours after stimulation to verify that hypertrophy had been induced. These cells can be assessed for hypertrophy in two different assays. Cells can be immunostained for sarcomeric myosin heavy chain with MF-20 monoclonal antibody (DEVELOPMENTAL STUDIES HYBRIDOMA BANK™) and cell size can be quantified by digital image capture and quantitative morphometry (see Xiang F, et al., Am J Physiol Heart Circ Physiol, 2006; 290(5):H1997-H2006). In addition, treated cells can be cultured in the presence of 3H-leucine to measure protein synthesis. After 24 hours of stimulation, cells can be pulse-labeled with 1.0 μCi/ml H-leucine for an additional 6 hours. The medium can be aspirated and the cells can be washed with ice-cold phosphate-buffered saline (PBS) and fixed on ice for 30 minutes with cold 10% trichloroacetic acid (TCA). After washing twice with 5% TCA, and once with water, the radioactivity incorporated into the TCA-precipitable material can be determined by liquid scintillation counting after solubilization in 0.25 M NaOH.

ROS induction and hypertrophic signaling can be assessed. To detect mitochondrial ROS, cultured neonatal myocytes can be stained with MITOSOX™ Red, a mitochondrial superoxide indicator, and MITOTRACKER® Green FM, a green-fluorescent mitochondrial stain, at baseline and after 48 hours of hypertrophic stimulation, according to the manufacturer's instructions. Cell lysates can also be analyzed by western blotting for appropriate phosphorylated and/or non-phosphorylated forms of kinases associated with different hypertrophic signaling pathways including, but not limited to, MAPKs, ERK1/2, JNK, p38, CaMKII, p70S6, AKT, gp130, erbB2, Ras, Rac1, and GSK-3β.

The apoptotic response to oxidative and endoplasmic reticulum stress in cultured neonatal mouse cardiomyocytes can be assessed. Cardiomyocytes can be prepared and cultured as described above for the assessment of their apoptotic response to oxidative and endoplasmic reticulum (ER) stress (see Liu Y, et al., Am J Physiol Heart Circ Physiol, 2010; 298(6):H2082-92 and Yu M, et al., OMICS, 2009; 13(6):501-11).

The cultured neonatal cardiomyocyte apoptotic response to oxidative stress can be tested by treatment with $H_2O_2$ (100 μM) for 24 hours. The apoptotic response to ER stress can also be tested by treating with tunicamycin (100 ng/ml) for 48 hours. After treatment, apoptotic cells can be detected using TUNEL staining to detect DNA fragmentation using, for example, a commercially available kit (ROCHE MOLECULAR DIAGNOSTICS™). Alternatively, cells can undergo Annexin V staining followed by flow cytometry. In brief, myocytes can be stained with Annexin V by using the Annexin-V-FLUOS™ staining kit (BECTON, DICKINSON AND COMPANY™). To exclude necrotic cells from the analysis, cells can also be incubated with propidium iodide. Cells can be analyzed (10,000 cells per sample) using a FACSCAN™ flow cytometer (BECTON, DICKINSON AND COMPANY™) with CELLQUEST™ flow cytometric analysis software. Propidium iodide-positive cells are necrotic and can be excluded from analysis.

Without being bound by any particular theory, it is anticipated that neonatal myocytes from TAZ-KD mice may demonstrate increased hypertrophy and increased ROS production after hypertrophic stimulation when compared to WT control cells. It is further predicted that increased ROS may be associated with increased signaling through the ERK and AKT pathways. Additionally, it is expected that TAZ-KD cardiomyocytes may be more susceptible to apoptosis induced by oxidative and ER stress.

Example 8—ROS Generation and Susceptibility to Cardiac Hypertrophy and Heart Failure May be Increased in TAZ-KD Mice Without being bound by any particular theory, it is hypothesized that TAZ-KD mice may demonstrate greater ROS generation and increased susceptibility to hypertrophy and heart failure after pressure overload or AngII infusion.

Hypertrophy may be induced by transverse aortic constriction or AngII infusion and heart tissue may be analyzed. Tafazzin-deficient mice reportedly develop diastolic dysfunction early (see Phoon C K L, et al., J Am Heart Assoc, 2012; 1(2):jah3-e000455-jah3-e) and systolic dysfunction relatively late (Acehan D, et al., J Biol Chem, 2011; 286 (2):899-908 and Soustek M S, et al., Hum Gene Ther, 2011; 22(7):865-71); however, their response to pressure-overload or AngII infusion appears to have not been studied. Late onset of cardiomyopathy in this model may suggest that other stressors may be involved, such as hypertension. TAZ-KD and WT mice can be raised to the age of 8-12 weeks and divided into 4 groups of 10 as follows: 1) WT, sham operation; 2) TAZ-KD, sham operation; 3) WT, aortic banding; and 4) TAZ-KD, aortic banding. Animals can undergo echocardiography followed by either aortic banding or sham operation (see Liu Y, et al., Am J Physiol Heart Circ Physiol, 2010; 298(6):H2082-92; Yu M, et al., OMICS, 2009; 13(6):501-11; and Liao R, et al., Circulation, 2002; 106(16):2125-31).

Mice can be anesthetized with avertin and then ventilated. The ascending aorta can be exposed by anterolateral thoracotomy and then constricted by tying a 7-0 silk suture around the aorta and a 27-gauge needle. Sham operated mice undergo thoracotomy but not aortic constriction. Mice can undergo serial echocardiography at 1, 2, 3, and 4 weeks, followed by euthanasia, harvesting of hearts, measurement of ventricular weight to body weight ratio, and measurement of ventricular weight to tibia length ratio followed by histology. Hypertrophy can also be induced by angiotensin II osmotic mini-pump infusion (see Xiang F, et al., Am J Physiol Heart Circ Physiol, 2006; 290(5):H1997-H2006), in 4 groups analogous to those described for TAC, with similar echocardiographic and gravimetric analysis.

Explanted hearts from treated animals can undergo routine histological analysis using standard stains such as hematoxylin/eosin and Masson's trichrome to observe for inflammation and fibrosis. Apoptosis can also be assessed using TUNEL staining. Oxidative stress can be assessed by immunostaining for 3-nitrotyrosine (3-NT), a potent marker of oxidative and nitrosative stress. F2-isoprostane levels can be measured within homogenized heart tissue, using LC-MS. F2-isoprostane detection is a sensitive marker of lipid peroxidation.

Without being bound by any particular theory, it is anticipated that TAZ-KD mice may develop more hypertrophy and worse heart failure after TAC or AngII compared to WT controls. Furthermore, increased fibrosis, apoptosis, 3-NT staining, and F2-isoprostane levels may be seen.

Example 9—Exogenous TAZ can Suppress Pathological Hypertrophy and Heart Failure In Vitro and In Vivo in Both TAZ-Deficient and WT Cells Fusion proteins have been engineered for uptake into cells and it has been shown that fusion proteins can augment defective mitochondrial respiration in both cultured cells and tafazzin-deficient hearts. Without being bound by any particular theory, it is hypothesized that administration of the peptides of the present disclosure can suppress ROS generation and ameliorate hypertrophy in both TAZ-deficient and wild-type cells. TAZ-KD and WT neonatal myocytes treated with hypertrophic stimuli can be concurrently treated with soluble tafazzin, with or without a CPP peptide. Similarly, TAZ-KD and WT mice undergoing aortic banding can be treated with soluble tafazzin, with or without a CPP peptide, administered systemically. Furthermore, it is predicted that TAZ with CPPs may suppress ROS generation, blunt the hypertrophic response, suppress apoptosis, and ameliorate heart failure.

Recombinant TAZ may have effects on hypertrophy and apoptosis in vitro. Neonatal myocytes from WT and TAZ-KD mice can be cultured and tested for hypertrophy, ROS generation, signal transduction, and apoptosis as described above. To assess the effectiveness of recombinant TAZ, cells induced with hypertrophic or apoptotic stimuli can be treated concurrently with recombinant TAZ, with or without a cell penetrating peptide at 10 µM/ml for 48 hours. Cell size, 3H-leucine uptake, induction of ROS, activation of signaling pathways, and induction of apoptosis can be tested as discussed above.

Recombinant TAZ may have effects on hypertrophy and heart failure in vivo. TAC or AngII infusion on WT and TAZ-KD mice can be performed, but it can be determined whether exogenous recombinant TAZ may rescue ROS generation and progression to hypertrophy and heart failure. Recombinant tafazzin can be systemically administered by retroorbital injection at weekly intervals or by prolonged infusion by osmotic minipump over 4 weeks. The effects of tafazzin on systolic and diastolic function can be assessed using echocardiography. Uptake into myocardium, effects on cardiolipin metabolism, mitochondrial respiration, oxidative stress, inflammation, fibrosis, and apoptosis can be assessed as described above.

Without being bound by any particular theory, it is expected that administration of recombinant TAZ to neonatal myocyte cultures may blunt the hypertrophic response, limit ROS generation, and decrease apoptosis in TAZ-KD cells. It is also expected that recombinant TAZ may improve these parameters in WT cells. It is predicted that systemic administration of tafazzin to tafazzin-deficient mice concurrently with TAC may lead to uptake into heart muscle, improved cardiolipin modification, improved mitochondrial respiration, reduced hypertrophy, heart failure, apoptosis, and fibrosis in TAZ-KD mice. Further, it is expected that local and systemic administration of tafazzin may improve diastolic and systolic dysfunction in tafazzin-deficient hearts. Additionally, it is expected that exogenous tafazzin may also improve these parameters in wild-type mice.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value, ±19% of the stated value, ±18% of the stated value, ±17% of the stated value, ±16% of the stated value, ±15% of the stated value, ±14% of the stated value, ±13% of the stated value, ±12% of the stated value, ±11% of the stated value, ±10% of the stated value, ±9% of the stated value, ±8% of the stated value, ±7% of the stated value, ±6% of the stated value, ±5% of the stated value, ±4% of the stated value, ±3% of the stated value, ±2% of the stated value, or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the description herein. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law.

Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Ed. or a dictionary known to those of ordinary skill in the art, such as the Oxford Dictionary of Biochemistry and Molecular Biology (Ed. Anthony Smith, Oxford University Press, Oxford, 2004).

It will be apparent to those having skill in the art that many changes may be made to the details of the above-described embodiments without departing from the underlying principles of the invention. The scope of the present invention should, therefore, be determined only by the following claims.

The invention claimed is:

1. A method for treating a subject having a cardiomyopathy, comprising:
   administering to the subject a fusion protein comprising a tafazzin peptide and a cellular permeability peptide.

2. The method of claim 1, wherein the cardiomyopathy is selected from at least one of chemotherapy-induced cardiomyopathy, diabetic cardiomyopathy, dilated cardiomyopathy, hypertensive cardiomyopathy, hypertrophic cardiomyopathy, ischemic cardiomyopathy, and noncompaction cardiomyopathy.

3. The method of claim 1, wherein the tafazzin peptide is coupled to the cellular permeability peptide by a polypeptide linker.

4. The method of claim 1, wherein the fusion protein is selected from the group consisting of SEQ ID NO:10, SEQ ID NO:11, and SEQ ID NO:12.

5. The method of claim 1, wherein the tafazzin peptide is selected from at least one of SEQ ID NO:1, SEQ ID NO:2, SEQ ID NO:3, SEQ ID NO:4, and SEQ ID NO:5.

6. The method of claim 1, wherein the cellular permeability peptide is selected from at least one of a cardiac targeting peptide, an antennapedia permeability peptide, an HIV Tat permeability peptide, and a Kaposi FGF4-permeability peptide.

7. The method of claim 1, wherein the cellular permeability peptide is a cardiac targeting peptide comprising SEQ ID NO:8.

8. The method of claim 1, wherein the cellular permeability peptide is an antennapedia permeability peptide comprising SEQ ID NO:6.

9. The method of claim 1, wherein the cellular permeability peptide is an HIV Tat permeability peptide comprising SEQ ID NO:7.

10. The method of claim 1, wherein the cellular permeability peptide is a Kaposi FGF4-permeability peptide comprising SEQ ID NO:9.

11. A method for treating a patient having a cardiomyopathy, comprising:
   administering to the patient an effective amount of a pharmaceutical composition comprising:
      a fusion protein comprising a tafazzin peptide and a cellular permeability peptide; and
      a pharmaceutically acceptable carrier
   to reduce a pathological effect or symptom of the cardiomyopathy.

12. The method of claim 11, wherein the cardiomyopathy is associated with a tafazzin gene (TAZ) mutation.

13. The method of claim 11, wherein the cardiomyopathy is selected from at least one of chemotherapy-induced cardiomyopathy, diabetic cardiomyopathy, dilated cardiomyopathy, hypertensive cardiomyopathy, hypertrophic cardiomyopathy, ischemic cardiomyopathy, and noncompaction cardiomyopathy.

14. The method of claim 11, wherein the tafazzin peptide is selected from at least one of SEQ ID NO:1, SEQ ID NO:2, SEQ ID NO:3, SEQ ID NO:4, and SEQ ID NO:5.

15. The method of claim 11, wherein the cellular permeability peptide is selected from at least one of a cardiac targeting peptide, an antennapedia permeability peptide, an HIV Tat permeability peptide, and a Kaposi FGF4-permeability peptide.

16. The method of claim 11, wherein the pathological effect or symptom of the cardiomyopathy is selected from at least one of dyspnea, heart enlargement, cardiac fibrosis, pulmonary congestion, peripheral edema, irregular heart rate, hypotension, and fatigue.

17. A method for prophylactically treating a patient at a risk of developing a cardiomyopathy, comprising:
   administering to the patient an effective amount of a pharmaceutical composition comprising:
      a fusion protein comprising a tafazzin peptide and a cellular permeability peptide; and
      a pharmaceutically acceptable carrier
   to reduce the risk of developing the cardiomyopathy.

18. The method of claim 17, wherein the tafazzin peptide is selected from at least one of SEQ ID NO:1, SEQ ID NO:2, SEQ ID NO:3, SEQ ID NO:4, and SEQ ID NO:5.

19. The method of claim 17, wherein the cellular permeability peptide is selected from at least one of a cardiac targeting peptide, an antennapedia permeability peptide, an HIV Tat permeability peptide, and a Kaposi FGF4-permeability peptide.

20. The method of claim 17, wherein the patient has a tafazzin gene (TAZ) mutation.

* * * * *